US012093815B2

(12) United States Patent
Otsuki et al.

(10) Patent No.: US 12,093,815 B2
(45) Date of Patent: Sep. 17, 2024

(54) LEARNING SYSTEM, REHABILITATION SUPPORT SYSTEM, METHOD, PROGRAM, AND TRAINED MODEL

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP); Makoto Kobayashi, Nisshin (JP); Masayuki Imaida, Ichinomiya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 232 days.

(21) Appl. No.: 16/875,390

(22) Filed: May 15, 2020

(65) Prior Publication Data

US 2020/0410339 A1    Dec. 31, 2020

(30) Foreign Application Priority Data

Jun. 27, 2019 (JP) ................................. 2019-120408

(51) Int. Cl.
*G06N 3/08* (2023.01)
*G06N 3/044* (2023.01)

(52) U.S. Cl.
CPC ............... *G06N 3/08* (2013.01); *G06N 3/044* (2023.01)

(58) Field of Classification Search
CPC .................................. G06F 3/08; G06F 3/0445
See application file for complete search history.

(56) References Cited

U.S. PATENT DOCUMENTS 10,130,311 B1 * 11/2018 De Sapio ............. A61B 5/7455
10,448,898 B2 * 10/2019 Tekumalla ............ G16H 50/30
(Continued)

FOREIGN PATENT DOCUMENTS

CN          109875834 A       6/2019
EP          3 649 940 A1      5/2020
(Continued)

OTHER PUBLICATIONS

Alvin Rajkomar et al, "Scalable and accurate deep learning with electronic health records", published in Digital Medicine (2018)1:18, and published online on May 8, 2018 at https://www.nature.com/articles/s41746-018-0029-1.pdf, and retrieved on Jul. 20, 2022. (Year: 2018).*

(Continued)

*Primary Examiner* — Shourjo Dasgupta
(74) *Attorney, Agent, or Firm* — Oliff PLC

(57) ABSTRACT

A learning unit of a learning system generates the following learning model. That is, this learning model is a model that inputs rehabilitation data for each predetermined period and predicts a change in index data, the rehabilitation data being data about rehabilitation performed by a trainee using a rehabilitation support system, the index data indicating at least one of a symptom, a physical ability, and a degree of recovery of the trainee. This rehabilitation data includes at least the index data and training data of the trainee, the training data being acquired during the rehabilitation in the rehabilitation support system. Further, the learning unit generates the learning model by using, as teacher data, data obtained in a period until the index data reaches a predetermined target level.

16 Claims, 15 Drawing Sheets

(56) References Cited

U.S. PATENT DOCUMENTS

| | | | |
|---|---|---|---|
| 10,937,333 B2* | 3/2021 | Maruyama | A61B 5/486 |
| 11,056,218 B2* | 7/2021 | Hu | G16H 10/60 |
| 11,263,523 B1* | 3/2022 | Duchon | G06N 3/0445 |
| 11,287,876 B2* | 3/2022 | Trim | G06F 3/011 |
| 11,387,000 B2* | 7/2022 | Saliman | G16H 10/60 |
| 11,507,179 B2* | 11/2022 | Lefaudeux | G06V 40/103 |
| 2011/0112808 A1* | 5/2011 | Anderson | G16H 50/50 703/2 |
| 2011/0245633 A1* | 10/2011 | Goldberg | A61B 5/165 600/323 |
| 2012/0290347 A1* | 11/2012 | Elazouni | G06Q 10/06313 705/7.12 |
| 2013/0172691 A1* | 7/2013 | Tran | A61B 5/0022 600/595 |
| 2013/0325508 A1* | 12/2013 | Johnson | G16H 10/60 705/3 |
| 2014/0143064 A1* | 5/2014 | Tran | A61B 5/01 705/14.66 |
| 2015/0012111 A1* | 1/2015 | Contreras-Vidal | A61B 5/369 623/25 |
| 2015/0342820 A1* | 12/2015 | Shimada | A63B 22/0087 482/69 |
| 2016/0287166 A1* | 10/2016 | Tran | A61B 5/74 |
| 2017/0027501 A1* | 2/2017 | Senanayake | A61B 5/1128 |
| 2017/0055918 A1* | 3/2017 | Hughes | H04L 43/028 |
| 2017/0156963 A1* | 6/2017 | Tuttemann | A61F 2/64 |
| 2017/0312579 A1 | 11/2017 | Nakashima | |
| 2019/0019578 A1* | 1/2019 | Vaccaro | G16H 40/63 |
| 2019/0066832 A1* | 2/2019 | Kang | A61B 5/1128 |
| 2019/0150792 A1 | 5/2019 | Nakashima et al. | |
| 2019/0266723 A1* | 8/2019 | Blanchard | G06V 20/698 |
| 2019/0283247 A1* | 9/2019 | Chang | A61B 5/1121 |
| 2020/0008712 A1 | 1/2020 | Takenaka | |
| 2020/0237291 A1* | 7/2020 | Sundaram | A61B 5/4833 |
| 2020/0402638 A1* | 12/2020 | Song | A61B 5/0022 |
| 2020/0410341 A1 | 12/2020 | Otsuki et al. | |
| 2021/0118557 A1* | 4/2021 | Pauws | G06N 7/005 |
| 2021/0383921 A1* | 12/2021 | Isobe | G16H 50/20 |

FOREIGN PATENT DOCUMENTS

| | | |
|---|---|---|
| JP | 2016-197330 A | 11/2016 |
| JP | 6052234 B2 | 12/2016 |
| JP | 2018-166640 A | 11/2018 |
| JP | 2019-092603 A | 6/2019 |
| WO | 2019/008657 A1 | 1/2019 |

OTHER PUBLICATIONS

Alireza Nejati, "Recursive (not Recurrent!) Neural Networks in TensorFlow", published Jun. 2016 at https://www.kdnuggets.com/2016/06/recursive-neural-networks-tensorflow.html, retrieved Jul. 20, 2022. (Year: 2016).*

Mohammad El-Nesr, "Imputing the Time-Series Using Python", published Dec. 31, 2018 at https://drnesr.medium.com/filling-gaps-of-a-time-series-using-python-d4bfddd8c460, retrieved Jul. 20, 2022. (Year: 2018).*

Selva Prabhakaran, "Time Series Analysis in Python—A Comprehensive Guide with Examples", published Feb. 13, 2019 at https://www.machinelearningplus.com/time-series/time-series-analysis-python, retrieved Jul. 22, 2022 (Year: 2019).*

IP dot com Search Result preview of "Prediction of Walking and Arm Recovery after Stroke: A Critical Review", published at Brain Sciences, Nov. 2, 2016, retrieved on Jan. 30, 2023. (Year: 2016).*

IP dot com Search Result preview of "Computational neurorehabilitation: modeling plasticity and learning to predict recovery", published at Journal of NeuroEngineering and Rehabilitation, Apr. 30, 2016, retrieved on Jan. 30, 2023. (Year: 2016).*

Aleksandar Jeremic et al, "Prediction Functional Independence Measure in Hip Fracture Events", publicly available via the 35th Annual International Conference of the IEEE EMBS, Osaka, Japan, Jul. 3-7, 2013, retrieved May 12, 2023. (Year: 2013).*

Fokke B. van Meulen et al, "Objective Evaluation of the Quality of Movement in Daily Life after Stroke", Frontiers in Bioengineering and Biotechnology, vol. 3, article 210, Jan. 2016, retrieved May 12, 2023. (Year: 2016).*

A Beaulieu et al, "Network of wireless medical devices to assess the gait of rehabilitation in patients for walking and running", published in 2017 Annual IEEE International Systems Conference, pp. 1-8, retrieved May 12, 2023. (Year: 2017).*

Roshanak Houmanfar et al, "Movement Analysis of Rehabilitation Exercises: Distance Metrics for Measuring Patient Progress", published in IEEE Systems Journal, vol. 10, No. 3, Sep. 2016, retrieved May 12, 2023. (Year: 2016).*

Thomas Seel et al, "Iterative Learning Control of FES-Assisted Gait", published Apr. 15, 2013 to https://www.mpi-magdeburg.mpg.de/1378126/Iterative-Learning-Control-of-FES-Assisted-Gait, retrieved May 12, 2023. (Year: 2013).*

Dylan Kobsar, etc., "Wearable Sensor Data to Track Subject-Specific Movement Patterns Related to Clinical Outcomes Using a Machine Learning Approach", published Aug. 27, 2018 in Sensors, retrieved Oct. 4, 2023. (Year: 2018).*

Athanasio I. Kyritsis, etc., "Gait Recognition with Smart Devices Assisting Postoperative Rehabilitation in a Clinical Setting", published Sep. 1, 2018, and made available at 2018 First International Conference on Artificial Intelligence for Industries, pp. 60-64, retrieved Oct. 4, 2023. (Year: 2018).*

Weijun Tao, etc., "Gait Analysis Using Wearable Sensors", published Feb. 16, 2012 in Sensors 2012, 12, 2255-2283, retrieved Oct. 4, 2023. (Year: 2012).*

Eni Halilaj, etc., "Machine learning in human movement biomechanics: Best practices, common pitfalls, and new opportunities" published in J Biomech. Nov. 16, 2018, 81: 1-11, retrieved Oct. 4, 2023. (Year: 2018).*

Zheng-An Zhu, etc., "Deep Learning for Sensor-Based Rehabilitation Exercise Recognition and Evaluation", published in Sensors 2019, 19, 887, retrieved Oct. 4, 2023. (Year: 2019).*

Luca Lonini, etc., "Activity Recognition in patients with lower limb impairments: Do we need training data from each patient?", published in 2016 38th Annual International Conference of the IEEE Engineering in Medicine and Biology Society, pp. 3265-3268, retrieved Oct. 4, 2023. (Year: 2016).*

Alvaro Muro-de-la-Herran, etc., "Gait Analysis Methods: An Overview of Wearable and Non-Wearable Systems, Highlighting Clinical Applications", published in Sensors 2014, 14, 3362-3394, retrieved Oct. 4, 2023. (Year: 2014).*

Fabian Horst, etc., "Explaining the Unique Nature of Individual Gait Patterns with Deep Learning", submitted to arXiv on Aug. 13, 2018, retrieved Oct. 4, 2023. (Year: 2018).*

S. Hochreiter and J. Schmidhuber, "Long Short-Term Memory," in Neural Computation, vol. 9, No. 8, pp. 1735-1780, Nov. 15, 1997.

Mar. 2, 2023 Office Action issued in U.S. Appl. No. 16/885,927.

U.S. Appl. No. 16/885,927, filed May 28, 2020 in the name of Nobuhisa Otsuki et al.

Aug. 10, 2023 Office Action issued in U.S. Appl. No. 16/885,927.
Dec. 11, 2023 Office Action issued in U.S. Appl. No. 16/885,927.
Apr. 19, 2024 Office Action issued in U.S. Appl. No. 16/885,927.

* cited by examiner

| DATA SET No. | SETTING PARAMETER | DETECTION DATA | TRAINEE DATA | STAFF DATA | CURRENT WALKING FIM | WALKING FIM CHANGE PATTERN (CORRECT-ANSWER LABEL) |
|---|---|---|---|---|---|---|
| 1 | parameter_1 | sensor_1 | USER_1 | PT1 | 1 | 3 |
| 2 | parameter_2 | sensor_2 | USER_2 | PT2 | 1 | 4 |
| 3 | parameter_3 | sensor_3 | USER_3 | PT3 | 3 | 2 |
| 4 | parameter_4 | sensor_4 | USER_4 | PT4 | 4 | 1 |
| ... | ... | ... | ... | ... | ... | ... |

Fig. 6

ID
LEARNING SYSTEM, REHABILITATION SUPPORT SYSTEM, METHOD, PROGRAM, AND TRAINED MODEL

CROSS REFERENCE TO RELATED APPLICATIONS

This application is based upon and claims the benefit of priority from Japanese patent application No. 2019-120408, filed on Jun. 27, 2019, the disclosure of which is incorporated herein in its entirety by reference.

BACKGROUND

The present disclosure relates to a learning system, a rehabilitation support system, a method, a program, and a trained model.

Trainees such as patients may use a rehabilitation support system such as a walking training apparatus when they perform rehabilitation. As an example of the walking training apparatus, Japanese Patent No. 6052234 discloses a walking training apparatus including a walking assistance apparatus that is attached to a leg of a trainee and assists the trainee in walking.

In some rehabilitation support systems, when a trainee performs rehabilitation, a training staff member such as a doctor or a physical therapist may attend the rehabilitation as an assistant for the trainee, give encouraging talks to the trainee, give a helping hand to the trainee, and/or perform a setting operation for the rehabilitation support system.

SUMMARY

Incidentally, in order to obtain good training results, the setting operation of the rehabilitation support system performed by the training staff member needs to be performed so that the rehabilitation support system can appropriately assist the trainee. Further, the timing of the setting operation, i.e., the timing at which assistance is added or ceased, or at which the degree of assistance is changed also affects the training results. Therefore, in order to perform such a setting operation, the training staff member needs to make a choice as to what kind of assistance should be given to the trainee, and determine an appropriate degree of the assistance and its timing. Further, the training staff member needs to determine what kind of encouraging talks he/she should give to the trainee and when he/she should give such talks to the trainee, and determine the timing at which he/she should give a helping hand to the trainee.

In order to appropriately support the above-described setting operation and the like, it is desirable that the training staff member recognizes beforehand index data of the trainee such as a symptom, a physical ability, and a degree of recovery of the trainee. Further, if it is possible to predict such index data in the future, it is possible to give more appropriate support.

The present disclosure has been made in order to solve the above-described problem and provides a learning system and the like that generates a learning model capable of predicting a change in index data of a trainee when the trainee performs rehabilitation using a rehabilitation support system.

A first exemplary aspect is a learning system including a learning unit configured to input rehabilitation data for each predetermined period and generate a learning model for predicting a change in index data, the rehabilitation data being data about rehabilitation performed by a trainee using a rehabilitation support system and including at least the index data and training data of the trainee, the index data indicating at least one of a symptom, a physical ability, and a degree of recovery of the trainee, the training data being acquired during the rehabilitation in the rehabilitation support system, in which the learning unit generates the learning model by using, as teacher data, data obtained in a period until the index data reaches a predetermined target level. In this way, it is possible to generate a learning model capable of predicting a change in index data of a trainee when the trainee performs rehabilitation by using the rehabilitation support system.

The learning system may further include an extraction unit configured to extract, from rehabilitation data of a plurality of trainees, rehabilitation data of a trainee whose condition indicated by the index data at an early stage of the training is at a predetermined level, in which the learning unit may be configured to generate the learning model for the trainee having the predetermined level by using the rehabilitation data extracted by the extraction unit as an input. In this way, it is possible to construct a learning model so that it can predict a change in index data of a trainee whose index data at an early stage of the training is at the predetermined level.

The extraction unit may also extract rehabilitation data of a trainee of which a combination of the index data at the early stage of the training and the index data at the time when it is at the predetermined level is a predetermined combination. In this way, it is possible to construct a learning model so that it can predict a change in index data of a trainee of which the index data at the early stage of the training and the index data at the current stage constitute a predetermined combination.

The training data may include a setting parameter in the rehabilitation support system that is used when the trainee performs the rehabilitation. In this way, it is possible to construct a learning model so that it can predict a change in index data while taking the setting parameter into consideration.

The rehabilitation data may include trainee data indicating a feature of the trainee. In this way, it is possible to construct a learning model so that it can predict a change in index data while taking the feature of the trainee into consideration.

The learning model may be a model for predicting a pattern of changes in the index data in which the index data gets closer to the predetermined target level. In this way, it is possible to construct a learning model capable of outputting a pattern of changes.

The learning model may be a model in which, in each of index levels indicated by the index data, a result of calculation at a one-level-different level (i.e., a level different from that level by one level) is recursively reflected. In this way, it is possible to construct a learning model capable of outputting a time point at which the index level changes.

In particular, the learning model may be a model including an RNN (Recurrent Neural Network). In this way, it is possible to construct a learning model by a general-purpose algorithm.

In particular, the learning model may be a model including an LSTM (Long Short-Term Memory) block. In this way, a gradient vanishing problem in a model including an RNN can be alleviated.

A second exemplary aspect is a rehabilitation support system capable of accessing a trained model, the trained model being a learning model trained by the learning system according to the first aspect, the rehabilitation support system including: a prediction unit configured to input rehabilitation data including at least the index data and the training data of a trainee who starts or is performing training to the trained model, and thereby predict the change in index data; and a presentation unit configured to show the change in index data predicted by the prediction unit. In this way, a training staff member who assists a trainee can give rehabilitation support while checking a result of a prediction of index data of the trainee when the trainee performs rehabilitation using the rehabilitation support system.

In particular, the second exemplary aspect may be a rehabilitation support system capable of accessing a trained model, the trained model being a learning model trained by the learning system including the extraction unit according to the first aspect, the rehabilitation support system including: a designation unit configured to designate the trainee; a prediction unit configured to input rehabilitation data including at least the training data of the trainee designated by the designation unit to a trained model corresponding to the index data of the trainee designated by the designation unit, and thereby predict the change in index data; and a presentation unit configured to show the change in index data predicted by the prediction unit. In this way, a training staff member who assists a trainee can give rehabilitation support while checking a change in index data predicted for a trainee whose index data at an early stage of the training is at the predetermined level when the trainee performs rehabilitation using the rehabilitation support system.

A third exemplary aspect is a learning method including a learning step of inputting rehabilitation data for each predetermined period and generating a learning model for predicting a change in index data, the rehabilitation data being data about rehabilitation performed by a trainee using a rehabilitation support system and including at least the index data and training data of the trainee, the index data indicating at least one of a symptom, a physical ability, and a degree of recovery of the trainee, the training data being acquired during the rehabilitation in the rehabilitation support system, in which in the learning step, the learning model is generated by using, as teacher data, data obtained in a period until the index data reaches a predetermined target level. In this way, it is possible to generate a learning model capable of predicting a change in index data of a trainee when the trainee performs rehabilitation by using the rehabilitation support system.

A fourth exemplary aspect is a method for supporting rehabilitation (a method for operating a rehabilitation support system) performed in a rehabilitation support system capable of accessing a trained model, the trained model being a learning model trained by the learning method according to the third aspect, the method including: a prediction step of inputting rehabilitation data including at least the index data and the training data of a trainee who starts or is performing training to the trained model, and thereby predicting the change in index data; and a presentation step of showing the change in index data predicted in the prediction step. In this way, a training staff member who assists a trainee can give rehabilitation support while checking a result of a prediction of index data of the trainee when the trainee performs rehabilitation using the rehabilitation support system.

A fifth exemplary aspect is a program for causing a computer to perform a learning step of inputting rehabilitation data for each predetermined period and generating a learning model for predicting a change in index data, the rehabilitation data being data about rehabilitation performed by a trainee using a rehabilitation support system and including at least the index data and training data of the trainee, the index data indicating at least one of a symptom, a physical ability, and a degree of recovery of the trainee, the training data being acquired during the rehabilitation in the rehabilitation support system, in which in the learning step, the learning model is generated by using, as teacher data, data obtained in a period until the index data reaches a predetermined target level. In this way, it is possible to generate a learning model capable of predicting a change in index data of a trainee when the trainee performs rehabilitation by using the rehabilitation support system.

A sixth exemplary aspect is a rehabilitation support program for a computer of a rehabilitation support system, the rehabilitation support system being capable of accessing a trained model, the trained model being a learning model trained by the program according to the fifth aspect, the rehabilitation support program being configured to cause the computer to perform: a prediction step of inputting rehabilitation data including at least the index data and the training data of a trainee who starts or is performing training to the trained model, and thereby predicting the change in index data; and a presentation step of showing the change in index data predicted in the prediction step. In this way, a training staff member who assists a trainee can give rehabilitation support while checking a result of a prediction of index data of the trainee when the trainee performs rehabilitation using the rehabilitation support system.

A seventh exemplary aspect is a trained model that is any one of learning models trained by the learning system according to the first aspect, the learning method according to the third aspect, and the program according to the fifth aspect. In this way, it is possible to generate a trained model capable of predicting a change in index data of a trainee when the trainee performs rehabilitation by using the rehabilitation support system.

According to present disclosure, it is possible to provide a learning system that generates a learning model capable of predicting a change in index data of a trainee when the trainee performs rehabilitation using a rehabilitation support system. Further, according to the present disclosure, it is possible to provide a rehabilitation support system using a generated trained model, a method and a program for training a trained model, a trained model, and a method and a program for rehabilitation support using a trained model.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 6 shows a table for explaining a data set for learning (hereinafter also referred to as learning data set) used in the learning process shown in FIG. 5;

DESCRIPTION OF EMBODIMENTS

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem.

First Embodiment

A first embodiment will be described hereinafter with reference to the drawings.

System Configuration

Figure 1:
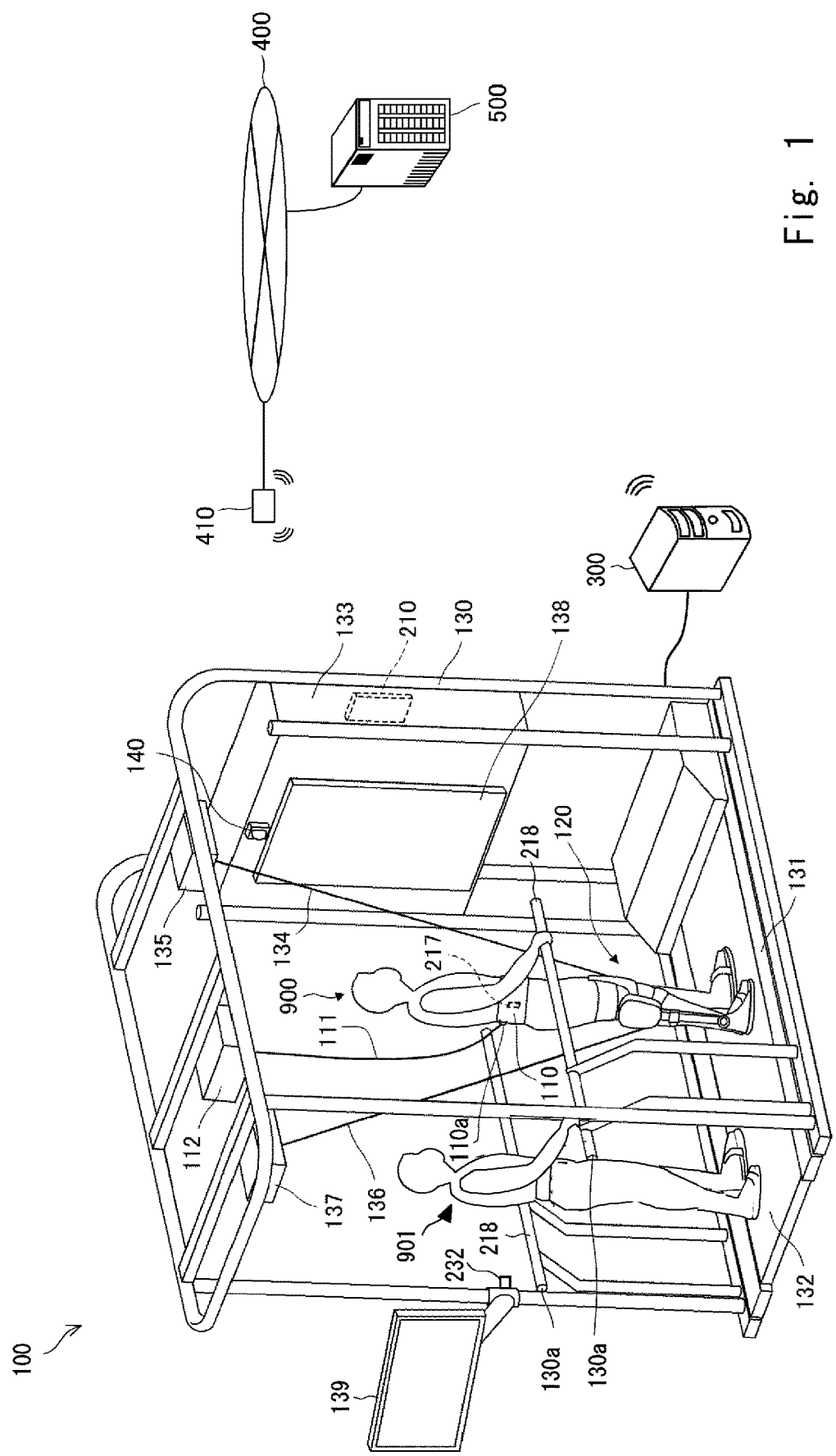
FIG. 1 is a general concept diagram showing an example of a configuration of a rehabilitation support system according to a first embodiment.

FIG. 1 is a general concept diagram showing an example of a configuration of a rehabilitation support system according to a first embodiment. The rehabilitation support system (the rehabilitation system) according to this embodiment mainly includes a walking training apparatus 100, an external communication apparatus 300, and a server (a server apparatus) 500.

The walking training apparatus 100 is a specific example of a rehabilitation support apparatus that supports rehabilitation performed by a trainee (a user) 900. The walking training apparatus 100 is an apparatus by which the trainee 900, who is, for example, a hemiplegic patient suffering from paralysis in one of his/her legs, does walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like. As shown as an example above, the training staff member 901 is a person(s).

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who does a walking training, gets on the belt 132 and tries walking in accordance with the movement of the belt 132. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height and width (i.e., distance therebetween). Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and/or moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The walking training apparatus 100 includes a fall-prevention harness apparatus as a safety apparatus, which includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on. Further, an emergency stop button 232 is provided near the management monitor 139. When the training staff member 901 pushes the emergency stop button 232, the walking training apparatus 100 immediately stops its operation.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

The overall control unit 210 generates rehabilitation data that may include setting parameters related to the training setting, various data related to the moving leg output from the walking assistance apparatus 120 as a result of training, and so on. The rehabilitation data may include, for example, data indicating the training staff member 901 or indicating his/her years of experience, level of proficiency, etc., data indicating the symptom, the walking ability, the degree of recovery, etc., of the trainee 900, various data output from sensors and the like provided outside the walking assistance apparatus 120. Note that details of the rehabilitation data will be described later.

The external communication apparatus 300 is a specific example of transmission means for transmitting the rehabilitation data to the outside. The external communication apparatus 300 may have a function of receiving and temporarily storing rehabilitation data output from the walking training apparatus 100 and a function of transmitting the stored rehabilitation data to the server 500.

The external communication apparatus 300 is connected to the control panel 133 of the walking training apparatus 100 through, for example, a USB (Universal Serial Bus) cable. Further, the external communication apparatus 300 is connected to a network 400 such as the Internet or an intranet through a wireless communication apparatus 410 by, for example, a wireless LAN (Local Area Network). Note that the walking training apparatus 100 may be equipped with a communication apparatus instead of using the external communication apparatus 300.

The server 500 is a specific example of the storage means for storing rehabilitation data. The server 500 is connected to the network 400 and has a function of accumulating rehabilitation data received from the external communication apparatus 300. The function of the server 500 will be described later.

In the first embodiment, the walking training apparatus 100 is described as an example of the rehabilitation support apparatus. However, the rehabilitation support apparatus is not limited to this example and may be a walking training apparatus having a different configuration. That is, the rehabilitation support apparatus may be an arbitrary rehabilitation support apparatus that supports rehabilitation performed by a trainee. For example, the rehabilitation support apparatus may be an upper-limb rehabilitation support apparatus that supports rehabilitation of a shoulder(s) or an arm(s). Alternatively, the rehabilitation support apparatus may be a rehabilitation support apparatus that supports rehabilitation for a balancing ability of a trainee.

Figure 2:
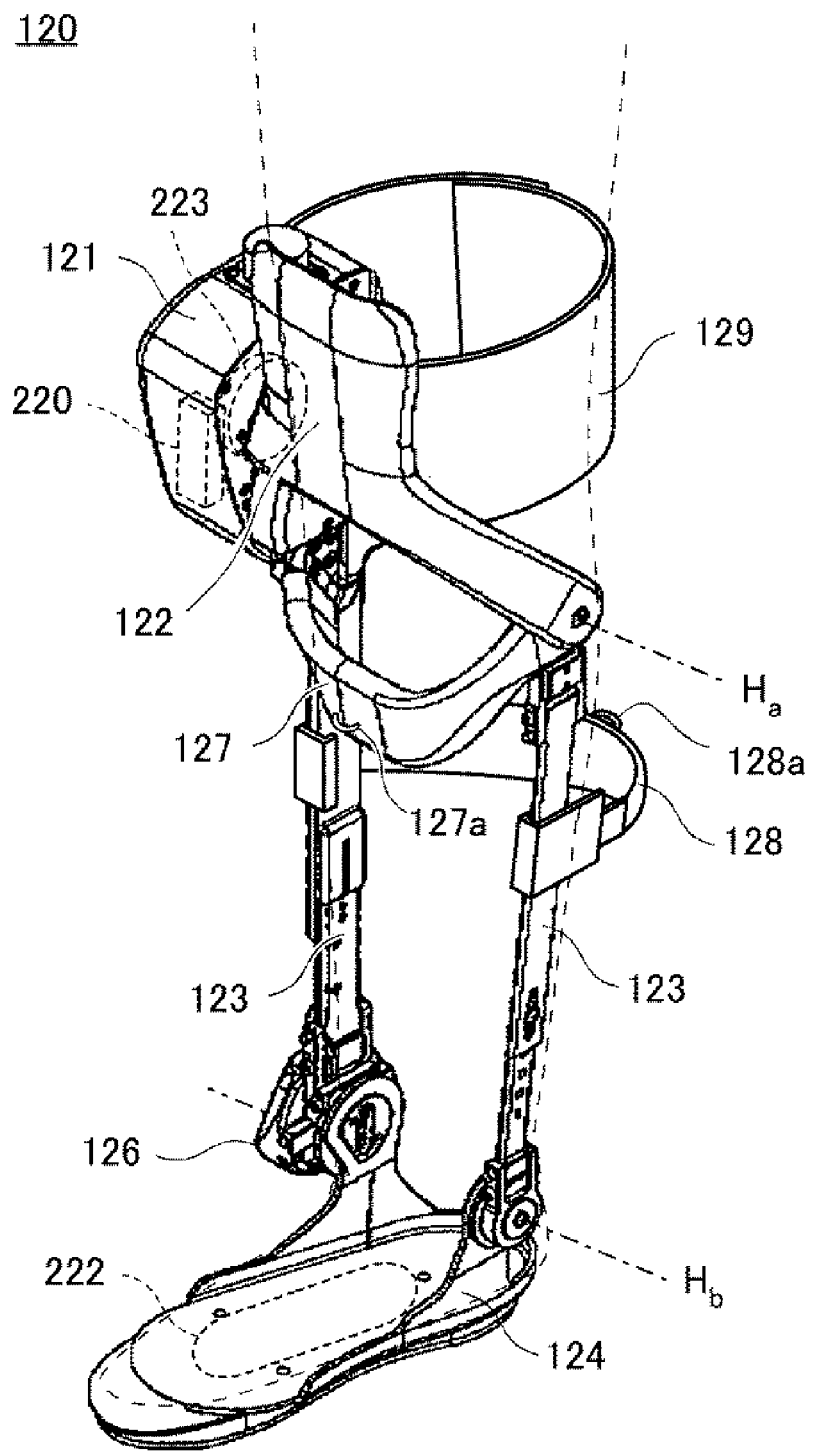
FIG. 2 is a schematic perspective view showing an example of a configuration of a walking assistance apparatus in the rehabilitation support system shown in FIG. 1.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the figure. The motor of the control unit 121 rotates according to an instruction from the assistance control unit 220, and by doing so, force the upper-leg frame 122 and the lower-leg frame 123 to open relative to each other around the hinge axis $H_a$ or force them to close relative to each other. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
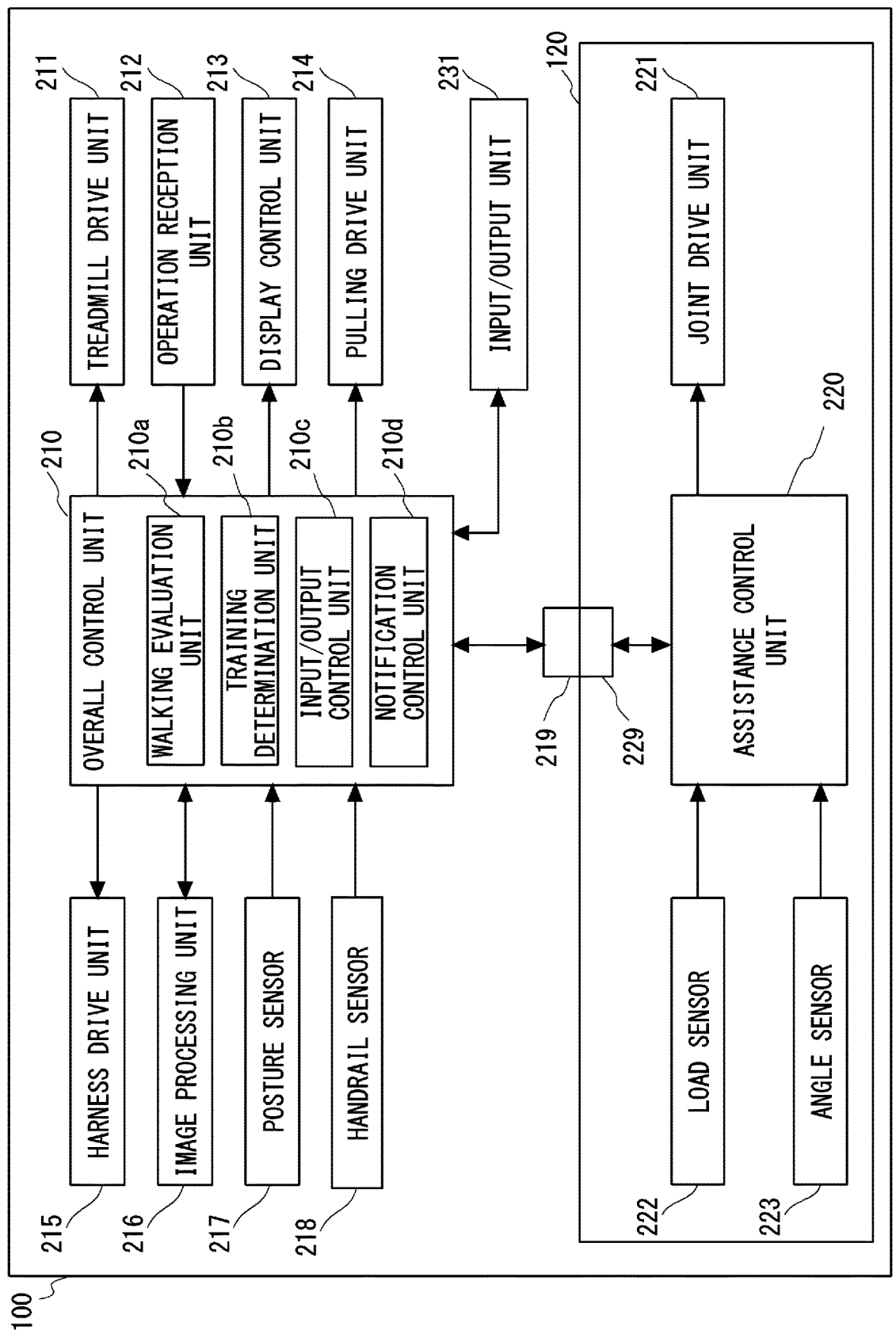
FIG. 3 is a block diagram showing an example of a system configuration of a walking training apparatus in the rehabilitation support system shown in FIG. 1.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input/output unit 231, and a walking assistance apparatus 120.

The overall control unit 210 is, for example, an MPU (Micro Processing Unit) and controls the overall operations of the apparatus by executing a control program loaded from a system memory. The overall control unit 210 may include a walking evaluation unit 210a, a training determination unit 210b, an input/output control unit 210c, and a notification control unit 210d, all of which will be described later.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130*a*. That is, the amount of the load corresponding to the part of the trainee's own weight that the trainee 900 cannot support by both legs is applied to the handrails 130*a*. The handrail sensor 218 detects this load and transmits a detection signal to the overall control unit 210.

The overall control unit 210 also serves as a function execution unit that performs various arithmetic operations and controls related to the overall control. The walking evaluation unit 210*a* evaluates whether the walking motion of the trainee 900 is abnormal or not by using data acquired from various sensors. The training determination unit 210*b* determines a training result of a series of walking trainings based on, for example, a cumulative number of the abnormal walking evaluated by the walking evaluation unit 210*a*. The overall control unit 210 can generate, as part of the rehabilitation data, a result of this determination or the cumulative number of the abnormal walking, based on which the determination result has been obtained.

Note that the determination method, including its criterion, is not limited to any particular methods. For example, the determination can be made by comparing an amount of movement of the paralyzed body part with a reverence value in each walking phase. Note that the walking phases are defined, for example, by classifying (i.e., dividing) one walking cycle of the diseased leg (or a normal leg) into a stance phase in a stance state, a transition phase from the stance phase to a swing phase in a swing state, the swing phase, a transition phase from the swing phase to the stance phase, etc. The walking phase can be classified (determined) based on, for example, the detection result of the load sensor 222 as described above. Note that although the walking cycle can be regarded as one cycle including a stance phase, a transitional phase, a swing phase, and another transitional phase as described above, any of these phases can be defined as the start phase. Alternatively, the walking cycle can be regarded as one cycle including, for example, a double-leg support state, a single-leg (diseased-leg) support state, a double-leg support state, and a single-leg (normal-leg) support state. Even in this case, any state may be defined as the start state.

Further, the walking cycle in which attention is paid to the right leg or the left leg (the normal leg or the diseased leg) can be further subdivided. For example, the stance phase can be divided into an initial ground contact and other four sub-phases, and the swing phase can be divided into three sub-phases. The initial ground contact means a moment when the observed foot touches the floor, and the four sub-phases of the stance phase means a load response phase, a mid-stance phase, a terminal stance phase, and a pre-swing phase. The load response phase is a period from the initial ground contact to when the opposite foot comes off the floor (opposite-foot-off). The mid-stance is a period from the opposite-foot-off to when the heel of the observed foot comes off the floor (heel-off). The terminal stance phase is a period from the heel-off to an initial ground contact on the opposite side. The pre-swing phase is a period from the initial ground contact on the opposite side to when the observed foot comes off the floor (foot-off). The three sub-phases of the swing phase mean an initial swing phase, a mid-swing phase, and a terminal swing phase. The initial swing phase is a period from the end of the pre-swing phase (the aforementioned foot-off) to when both feet cross each other (foot crossing). The mid-swing phase is a period from the foot crossing to when the tibia becomes vertical (vertical tibia). The terminal swing phase is a period from the vertical tibia to the next initial ground contact.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program according to an instruction from the overall control unit 210. Further, the assistance control unit 220 notifies the overall control unit 210 of the state of the walking assistance apparatus 120 through the communication connection IFs 229 and 219. Further, the assistance control unit 220 performs control of walking assistance apparatus 120, such as the start/stop thereof, in response to a command from the overall control unit 210.

The joint drive unit 221 includes a motor of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The load sensor 222 detects the magnitude and the distribution of the vertical load (e.g., the vertical pressure) applied to the sole of the trainee 900 and transmits a detection signal to the assistance control unit 220 as described above. The assistance control unit 220 receives and analyzes the detection signal, and thereby determines the swing/stance state and estimates the switching therebetween.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

The input/output unit 231 includes, for example, a USB (Universal Serial Bus) interface and is a communication interface for connecting to an external apparatus (an external communication apparatus 300 or other external apparatus). The input/output control unit 210c of the overall control unit 210 communicates with the external apparatus through the input/output unit 231, rewrites the above-described control program stored in the overall control unit 210 and the control program stored in the assistance control unit 220, receives commands, outputs generated rehabilitation data, and so on. The walking training apparatus 100 communicates with the server 500 through the input/output unit 231 and the external communication apparatus 300 under the control of the input/output controller 210c. For example, the input/output control unit 210c can control the transmission of rehabilitation data to the server 500 and the reception of a command from the server 500 through the input/output unit 231 and the external communication apparatus 300.

When it is necessary to provide a notification to the training staff member 901, the notification control unit 210d provides the notification from the management monitor 139 or a separately-provided speaker(s) by controlling the display control unit 213 or a separately-provided sound control unit or the like. The situation in which it is necessary to provide a notification to the training staff member 901 may include a situation in which a command for providing a notification is received from the server 500. Details of this notification will be described later.

Next, the server 500 will be described in detail. As described above, the walking training apparatus 100 transmits various rehabilitation data to the server 500 through the external communication apparatus 300. The server 500 may be configured so as to receive rehabilitation data from a plurality of walking training apparatuses 100. In this way, the server 500 can collect a number of rehabilitation data. Further, the server 500 is a processing apparatus that processes various data. For example, the server 500 can function as a learning apparatus (a learning system) that constructs a trained model by performing machine learning by using collected rehabilitation data. The learning apparatus can also be a learning machine. Note that the learning apparatus may also be referred to as a learning model generation apparatus.

Figure 4:
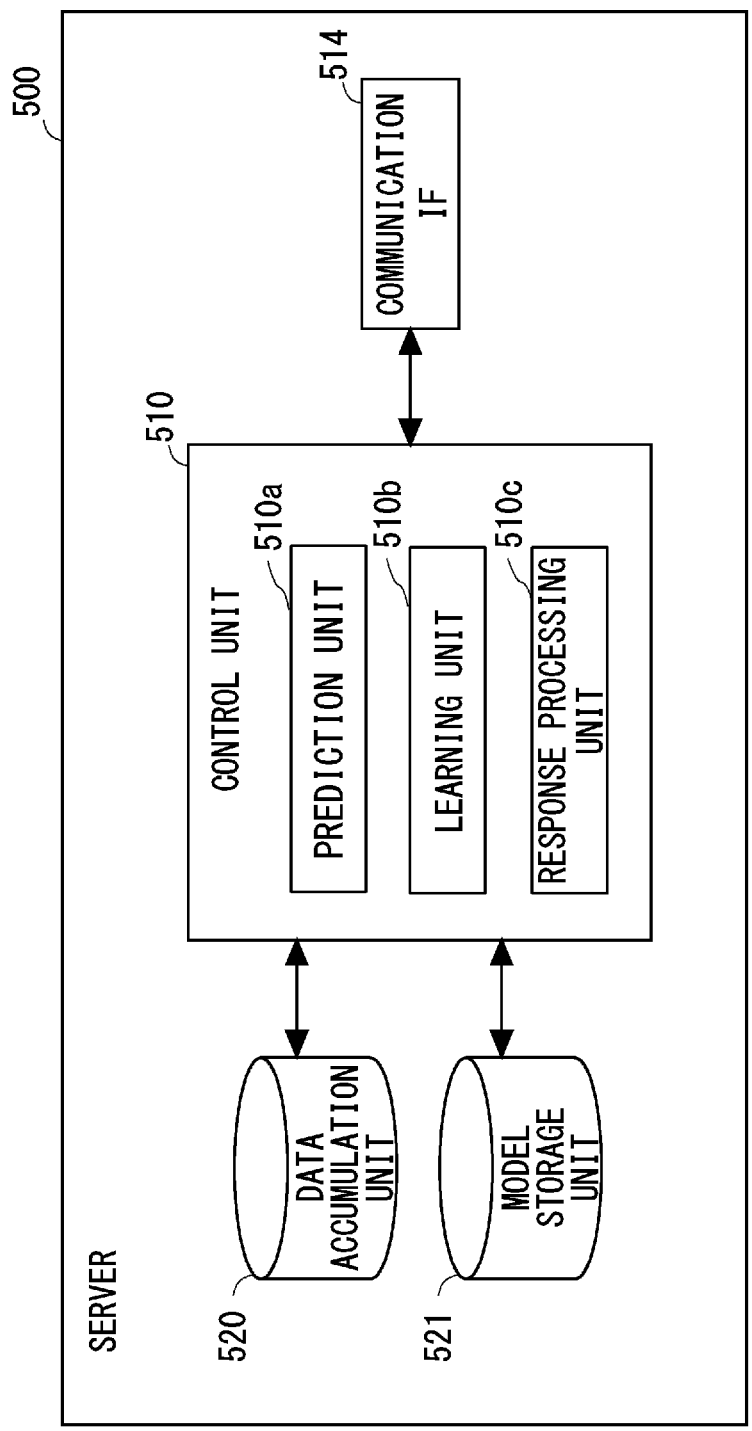
FIG. 4 is a block diagram showing an example of a configuration of a server in the rehabilitation support system shown in FIG. 1.

FIG. 4 is a block diagram showing an example of a configuration of the server 500. As shown in FIG. 4, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 may include a prediction unit 510a, a learning unit 510b, and a response processing unit 510c, which will be described later. Further, in such a case, the above-described control program includes a program(s) for implementing functions of the control unit 510 including functions of the aforementioned parts 510a to 510c.

The communication IF 514 includes, for example, a wired LAN interface and is a communication interface for connecting to the network 400. The control unit 510 can receive rehabilitation data from the walking training apparatus 100 and transmit a command to the walking training apparatus 100 through the communication IF 514.

The data accumulation unit 520 includes a storage device such as an HDD (Hard Disk Drive) or an SSD (Solid State Drive) and stores rehabilitation data therein. The control unit 510 writes the rehabilitation data received from the external communication apparatus 300 into the data accumulation unit 520 through the communication IF 514.

Similarly, the model storage unit 521 includes a storage device such as an HDD or an SSD. Note that the data accumulation unit 520 and the model storage unit 521 may include (i.e., share) a common storage device. The model storage unit 521 stores at least one of a learning model that has not been trained yet (including those under training) (hereinafter referred to as an untrained model) and a learning model that has been already trained (hereinafter referred to as a trained model). When the server 500 functions as a learning apparatus, at least an untrained model is stored in the model storage unit 521. When the server 500 performs a rehabilitation support process in cooperation with the walking training apparatus 100, at least an operable trained model is stored in the model storage unit 521.

Further, the control unit 510 may be configured so as to perform control to switch between a function as a learning apparatus and a function for performing a rehabilitation support process (including a process for showing a result of a prediction) by using a trained model. Note that the servers 500 may be distributed to (or divided into) an apparatus that is used in a learning stage and an apparatus that is used in an operation stage in which a trained model is used. The learning unit 510b is provided in order to enable the server 500 to function as a learning apparatus. Further, the prediction unit 510a and the response processing unit 510c are provided in order to enable the server 500 to perform a part of the rehabilitation support process.

Rehabilitation Data

Prior to describing the prediction unit 510a, the learning unit 510b, and the response processing unit 510c, rehabilitation data that the server 500 can collect for learning or for a rehabilitation support process is described hereinafter. The rehabilitation data that the server 500 can collect mainly includes (1) setting parameters of the walking training apparatus 100, (2) detection data detected by sensors and the like provided in the walking training apparatus 100, (3) data related to the trainee 900, and (4) data related to the training staff member 901. The rehabilitation data of the above-described items (1) to (4) may be collected in association with their acquisition date. Further, the detection data or the setting parameter may be collected as time-series log data, or may be, for example, feature values extracted from data acquired at certain time intervals.

The rehabilitation data is mainly data that is obtained by an input operation, an automatic input, a measurement by a sensor, or the like in the walking training apparatus 100. Further, the rehabilitation data may also include recorded image data recorded by the camera 140. Note that the rehabilitation data may be data acquired on each day of rehabilitation. In this case, the rehabilitation data can be referred to as daily report data. In the following description, it is assumed that the server 500 collects rehabilitation data generated by the walking training apparatus 100. However, it is also possible to configure the server 500 so as to acquire a part of rehabilitation data from an apparatus other than the walking training apparatus 100 such as another server. Here, the part of the rehabilitation data may be, for example, a detail of data of the above-described item (3) such as a symptom of the trainee 900, or a detail of data of the above-described item (4) such as years of experience of a PT (Physical Therapist). The former can be stored in other servers as medical record information of the trainee 900 and the latter can be stored in other servers as a personal history of a PT.

In the learning stage, the server 500 may receive rehabilitation data from the walking training apparatus 100 when new rehabilitation data is generated or at regular intervals such as on every day or in every week. The type of rehabilitation data to be used (the content included in rehabilitation data) in the learning stage may be changed from that in the operation stage. For example, in the operation stage, the server 500 may receive rehabilitation data from the walking training apparatus 100 at the start of training, and may receive data of the above-described items (1) to (4) that is changed during the training. Further, the transmission and the reception of rehabilitation data may be initiated by either the walking training apparatus 100 or the server 500.

The above-described item (1) is described.

The data of the above-described item (1) can be defined as training data of the trainee 900 that is acquired during rehabilitation in the walking training apparatus 100 together with the detection data of the above-described item (2).

The setting parameter of the walking training apparatus 100 is, for example, data that is input by an operator or automatically set in order to define the actions performed by the walking training apparatus 100. Note that as described above, it is assumed that the operator is typically the training staff member 901 who actually attends the training of the trainee 900. Therefore, the following description is given on the assumption that the operator is the training staff member 901. Further, the training staff member 901 is often a PT (Physical Therapist). Therefore, the training staff member 901 may also be referred to simply as the "PT" in the following description.

In the walking training apparatus 100, the level of difficulty of walking training can be adjusted by the setting parameters. Note that the setting parameters may include a parameter indicating the level of difficulty, and in this case, some or all of the other setting parameters may be changed according to the change in the level of difficulty. The training staff member 901 increases the level of difficulty of the walking training as the trainee 900 recovers. That is, the training staff member 901 reduces the assistance provided by the walking training apparatus 100 as the walking ability of the trainee 900 improves. Further, the training staff member 901 increases the assistance when an abnormality is found during the walking training. As the training staff member 901 appropriately adjusts the setting parameters, the trainee 900 can perform appropriate walking training and hence perform the rehabilitation more efficiently.

Specific examples of the setting parameters are shown hereinafter.

Examples of the setting parameters include a partial weight-supported amount [%], vertical positions of the handrails 130a [cm], left/right positions of the handrails 130a [cm], presence/absence of a hip joint, ankle joint plantar flexion limitation [deg], and ankle joint dorsiflexion limitation [deg]. Further, the examples of the setting parameters also include a treadmill speed [km/h], swinging assistance [level], and a swinging forward/backward ratio [forward/backward]. Further, the examples of the setting parameters also include knee extension assistance [level], a knee flexing angle [deg], a knee flexing/extending time [sec], a wedge thickness (or a shoe lift) [mm], a weight-off threshold [%], and a load threshold [%]. Further, the examples of the setting parameters also include an inclination of the belt of the treadmill [deg], assistance for a motion of a joint by the walking assistance apparatus [level], a frequency with which assistance for a motion of a joint or swinging assistance by the walking assistance apparatus is provided, a condition for determining abnormal or normal walking (e.g., a determination threshold), a condition for determining that the trainee will fall down or is likely to fall down (e.g., a determination threshold), and a condition for an occurrence of abnormal or normal walking in the case where a notification is provided in association with the abnormal or normal walking (a frequency of occurrences, an occurrence threshold, etc.). Note that the notification may be any of a sound, a vibration, a display, or the like, and may include some or all of them. Note that any type of unit may be used as the unit of data included in rehabilitation data, including the above-shown setting parameters.

The partial weight-supported amount is a ratio at which the weight of the trainee 900 is supported by making the harness pulling unit 112 pull the harness wire 111. The training staff member 901 sets the partial weight-supported amount to a lower value as the desired level of difficulty of the walking training increases. The vertical positions and the left/right positions of the handrails 130a are amounts of adjustments of the handrails 130a from reference positions. The presence/absence of a hip joint is whether or not the hip joint is attached. The ankle joint plantar flexion limitation and the ankle joint dorsiflexion limitation define an angular range in which the lower-leg frame 123 and the sole frame 124 can rotate around the hinge axis $H_b$. The ankle joint plantar flexion limitation corresponds to an upper-limit angle on the front side and the ankle joint dorsiflexion limitation corresponds to a maximum angle on the rear side. That is, the ankle joint plantar flexion limitation and the ankle joint dorsiflexion limitation are limit values of angles at which the ankle joint is bent in a direction in which the toe is lowered and a direction in which the toe is raised, respectively. The training staff member 901 sets the values of the ankle joint plantar flexion limitation and the ankle joint dorsiflexion limitation so that the angular range increases as the desired level of difficulty of the walking training increases.

The treadmill speed is a walking speed on the treadmill 131. The training staff member 901 sets the treadmill speed to a higher value as the desired level of difficulty of the walking training increases. The swinging assistance is a level corresponding to the pulling force applied by the front wire 134 when the leg is swung. Further, the maximum pulling force is increased as this level is raised. The training staff member 901 sets the swinging assistance to a lower level as the desired level of difficulty of the walking training increases. The swinging forward/backward ratio is a ratio between the pulling force by the front wire 134 and the pulling force by the rear wire 136 when the leg is swung.

The knee extending assistance is a level corresponding to the driving torque of the joint drive unit 221 that is applied to prevent the knee from buckling during the stance state. Further, the driving torque is increased as this level is raised.

The training staff member 901 sets the knee extending assistance at a lower level as the desired level of difficulty of the walking training increases. The knee flexing angle is an angle at which knee extending assistance is provided. The knee flexing/extending time is a period during which the knee extending assistance is provided. Further, when this value is large, the knee is assisted so that it is slowly flexed and extended, whereas when this value is small, the knee is assisted so that it is quickly flexed and extended.

The wedge thickness is a height of a member such as a cushion provided in the sole of the shoe of the leg of the trainee 900 opposite to the paralyzed leg thereof (i.e., the leg on the side on which the walking assistance apparatus 120 is not attached). The weight-off threshold is one of the thresholds for the load (i.e., the pressure) applied to the sole. When the load becomes smaller than this threshold, the swinging assistance is cancelled (i.e., ceased). The load threshold is one of the thresholds for the load applied to the sole. When the load exceeds this threshold, the swinging assist is provided (i.e., started). As described above, the walking assistance apparatus 120 may be configured so that the flexing/extending motion of the knee can be adjusted by four setting parameters, i.e., the knee flexing angle, the knee flexing/extending time, the weight-off threshold, and the load threshold.

Further, the walking training apparatus 100 may also be configured so that setting values of various parameters such as a load and an angle, a target value, a target achievement rate, a target achievement timing, etc. are fed back to the trainee and/or training staff member by a sound output from a speaker(s) (not shown). The above-described setting parameters may include parameters for other settings such as presence/absence of a feedback sound and its volume.

Further, the above-described setting parameters may not be setting parameters directly related to the level of difficulty of the training. For example, the above-described setting parameters may be setting values for images, music, a type of game, a level of difficulty of game, etc. that are provided through the training monitor 138 or a speaker(s) (not shown) in order to motivate the trainee 900.

Note that the above-described setting parameters are merely examples and other setting parameters may be used. Further, some of the above-described setting parameters may not be used. Further, although the above-described setting parameters include many parameters for adjusting the level of difficulty of the training as described above, they may also include parameters unrelated to the level of difficulty. For example, the walking training apparatus 100 may be configured so as to display an alert icon image that is to be displayed on the training monitor 138. Further, examples of the setting parameters unrelated to the level of difficulty include parameters for increasing the degree of concentration of the trainee 900 on the training, such as the size and the displaying interval of the above-described alert icon image. Further, time information such as date and time at which the setting operation is performed or timing information other than the time (e.g., information indicating a distinction between the stance phase, the swing phase, etc. in one walking cycle) can be added to the above-described setting parameters.

The above-described item (2) is described.

The detection data of the above-described item (2) can be defined as training data of the trainee 900 that is acquired during the rehabilitation in the walking training apparatus 100 together with the data of the above-described item (1).

A typical example of the detection data is sensor data. The sensor data is sensor values detected by various sensors of the walking training apparatus 100. For example, the sensor data includes an inclination angle of the trunk detected by the posture sensor 217, a load and an inclination angle detected by the handrail sensor 218, an angle detected by the angle sensor 223, etc. The sensors that output the sensor data are an acceleration sensor, an angular-velocity sensor, a position sensor, an optical sensor, a torque sensor, a weight sensor, etc. Further, encoders provided in motors of the winding mechanisms or the like of the front wire 134, the rear wire 136, and the harness wire 111 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 900 by performing image processing based on an image taken by shooting at least an area including the eyes of the trainee 900, or obtained by determining the orientation (upward/downward etc.) of the face of the trainee 900 based on an image taken by shooting at least the face. Such data may also be included in the aforementioned detection data. Further, the detection data may be audio data (voice data) acquired by a voice acquisition unit, such as a microphone, that acquires a voice of the trainee 900 or the training staff member 901, text data obtained by performing a voice analysis on the voice data, or data obtained by analyzing the text data. The voice of the training staff member 901 may include an encouraging talk to the trainee 900 about, for example, how to correct his/her walking. Further, the sensor data may be data obtained by detecting brain waves of the trainee 900 by using an electroencephalograph, or may be data obtained by detecting brain waves of the training staff member 901 by using an electroencephalograph.

Further, the line-of-sight detection sensor, a shooting unit that takes the above-described image, a microphone, and the like can be disposed in the walking training apparatus 100 itself. Alternatively, they can also be disposed in, for example, an eyeglass-type wearable terminal that is worn by the trainee 900. This terminal may include a wireless communication unit that wirelessly transmits and receives data by a wireless communication technique such as Bluetooth (Registered Trademark). Further, the walking training apparatus 100 may also include a wireless communication unit. In this way, the walking training apparatus 100 can acquire data acquired by the wearable terminal through wireless communication. Although the electroencephalograph is limited to those having high detection accuracy, it may be disposed in the walking training apparatus 100 itself and configured so that the electroencephalogram of the trainee 900 and that of the training staff member 901 can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as a sensor, is not limited to those described above with reference to FIGS. 1 to 3 or those exemplified by the eyeglass-type wearable terminal. For example, the trainee 900 may wear clothes equipped with a wearable biosensor and/or a wearable touch sensor. Here, the clothes are not limited to those worn on the upper body. That is, they may be those worn on the lower body, a top-and-bottom set, or those attached to a part of the harness 110 or the like.

Further, a wireless communication unit like the one described above is provided in each of the clothes and the walking training apparatus 100. In this way, the walking training apparatus 100 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 900, who is the wearer, made from the outside. That is, the wearable touch sensor can acquire data indicating information about a position where the training staff member 901 touched the trainee 900.

Further, the detection data is not limited to the values indicated by the detection signals detected by various sensors and the like. That is, they may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame 122 and the lower-leg frame 123 detected by the angle sensor 223. Further, the sensor data of the angle sensor may include an angular velocity that is obtained by differentiate the angle. The sensor data of the acceleration sensor may be a velocity that is obtained by integrating the acceleration or a position that is obtained by integrating the acceleration twice.

For example, the detection data may include the below-described average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill 131 or a value calculated from the drive signal in the treadmill drive unit 211. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff member 901 has assisted the trainee 900 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times]. Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill 131 that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the above-described detection data may not be used. That is, when the detection data is used as rehabilitation data, all that the server 500 has to do is to collect at least one detection data.

The above-described item (3) is described.

The data related to the trainee 900 (hereinafter referred to as trainee data) indicates, for example, a property of the trainee 900. Examples of the trainee data include an age, a gender, a physique (a height, a weight, etc.) of the trainee 900, information about a symptom, a Br. Stage, an SIAS, an initial walking FIM, and a latest walking FIM. Further, the trainee data may also include a name or an ID of the trainee 900. Further, the trainee data may also include preference information indicating a preference of the trainee 900 and personality information indicating his/her personality. Further, the trainee data may include, as the FIM, an exercise item other than those related to the walking ability, and may include a recognition item. That is, the trainee data may include various data indicating physical abilities of the trainee 900. Note that part or all of the trainee data may be referred to as body information, basic information, or trainee feature information.

Note that the symptom information may include information indicating an initial symptom, a time when the symptom appears, and a current symptom. Further, it can be considered that the trainee 900 needs to perform rehabilitation mainly because of at least one of the symptoms described above. However, symptoms that are unlikely to be directly related to the rehabilitation may also be included in the symptom information. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc.

The Br. Stage means a Brunnstrom Recovery Stage in which a recovery process of a hemiplegia is divided into six stages based on the observation. The trainee data may include, of the Br. Stage, lower-limb items that are main items related to the walking training apparatus 100. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

For example, a walking FIM is a general index indicating the degree of recovery. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 900 gradually increases. Note that the walking distance in the evaluation of the walking FIM is not limited to 50 m. For example, the walking distance may be 15 m.

As can be understood from the above description, the latest walking FIM used by the walking training apparatus 100 is used as not only an index indicating the physical ability of the trainee 900 but also an index indicating the degree of recovery of the trainee 900 from the start of the rehabilitation. The walking FIM is used as an index indicating the moving ability of the trainee 900 when no actuator is used, i.e., an index indicating his/her walking ability. In other words, the walking FIM is an important index in order to recognize the progress of the rehabilitation of the trainee 900. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee 900 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

As described above, the trainee data in the above-described item (3) may include index data about rehabilitation performed by the trainee 900 by using the walking training apparatus 100, including at least one of the symptom, the physical ability, and the degree of recovery of the trainee 900. For example, the degree of recovery may be a walking FIM, a walking speed on a level ground, an SIAS, or the like, but is not limited to such examples. Further, the physical ability may include the presence/absence of a cane in addition to the aforementioned examples. Note that in general, data that can be included in both concepts of the physical ability and the degree of recovery, such as the latest walking FIM, may be included in one of them. However, such data can also be included in both of them. For example, the above-described index data can be handled as rehabilitation data that is not included in the trainee data of the above-described item (3), or can be handled as both of the trainee data of the above-described item (3) and the data that is not included therein. Note that the same applies to all the items of the rehabilitation data. Further, data of a given item can be handled as data of one or a plurality of the above-described items (1) to (4). Further, time information such as the date and time at which the walking FIM is acquired, e.g., the measurement date of the walking FIM may be added in the above-described trainee data.

The above-described item (4) is described.

The data about the training staff member 901 (hereinafter referred to as staff data) indicates, for example, a property of the training staff member 901. The staff data includes a name or an ID, an age, a gender, a physique (a height, a weight, etc.) of the training staff member 901, a name of a hospital to which the training staff member 901 belongs, and his/her years of experience as a PT or a doctor. The staff data may include, as data related to the assistance, a value that numerically represents the timing at which the trainee 900 is assisted.

Further, in the case where a plurality of training staff members simultaneously assist the rehabilitation, the rehabilitation data may include data of the plurality of staff members. Further, each staff data may include information indicating whether the staff member is the main training staff member or an assistance training staff member. In addition to or instead of such information, each staff data may include information indicating whether the staff member is a training staff member who performs a setting operation and/or image checking in the management monitor 139, or whether or not the staff member is a training staff member who just physically supports the trainee 900 by hand.

Further, the walking training apparatus 100 may be configured so that a user (e.g., a training staff member) can enter a rehabilitation plan for the trainee 900. Further, the data of the rehabilitation plan entered as described above may also be included as staff data related to the training staff member 901 who has entered the data or as rehabilitation data belonging to other categories. Further, the walking training apparatus 100 may be configured so that, to make it possible to cope with the change of the training staff member 901, a user can enter remarks and/or messages for assisting the training of the trainee 900 in the future. Further, the data entered as described above may also be included as staff data related to the training staff member 901 who has entered the data or as rehabilitation data belonging to other categories.

The reason for including these data in the rehabilitation data is that there are possible situations where a training staff member has been able to successfully carry out the training of the trainee 900 because of the presence of remarks and/or messages given by other skilled training staff members. Further, time information such as the date and time at which the rehabilitation plan is entered, e.g., the input date and time of the rehabilitation plan may be added in the above-described staff data.

Learning Stage: Construction of Learning Model

Figure 5:
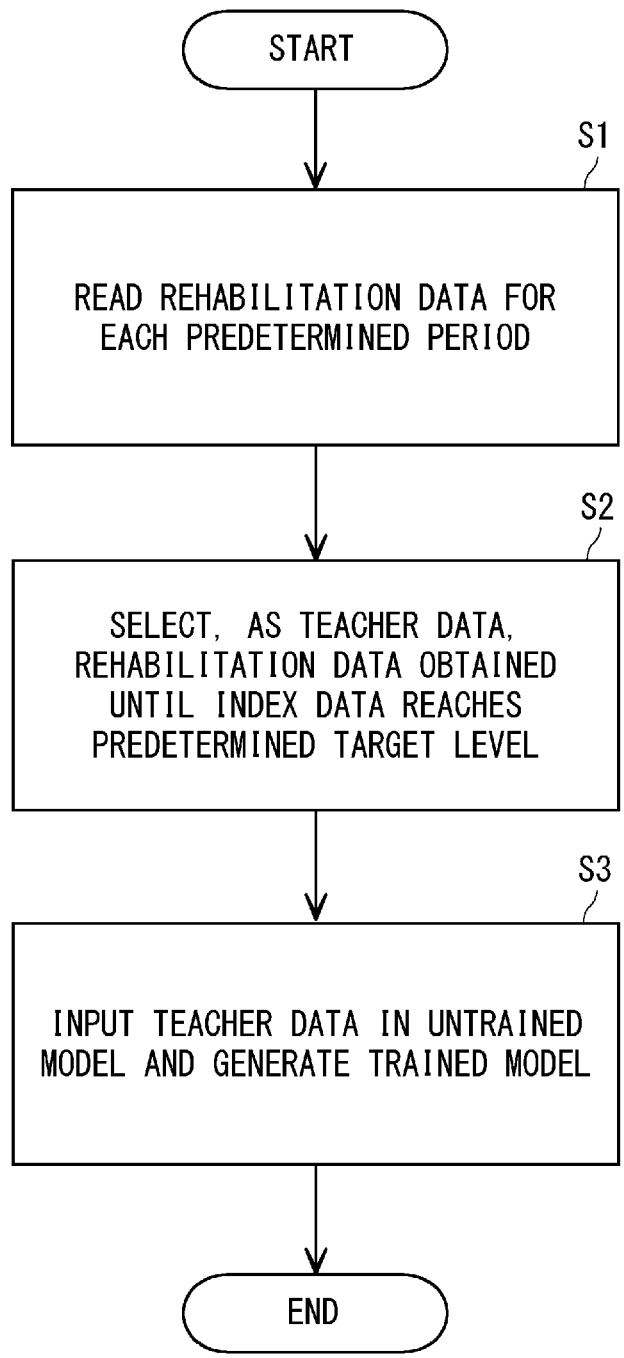
FIG. 5 is a flowchart for explaining an example of a learning process performed by the server shown in FIG. 4.
Figure 7:
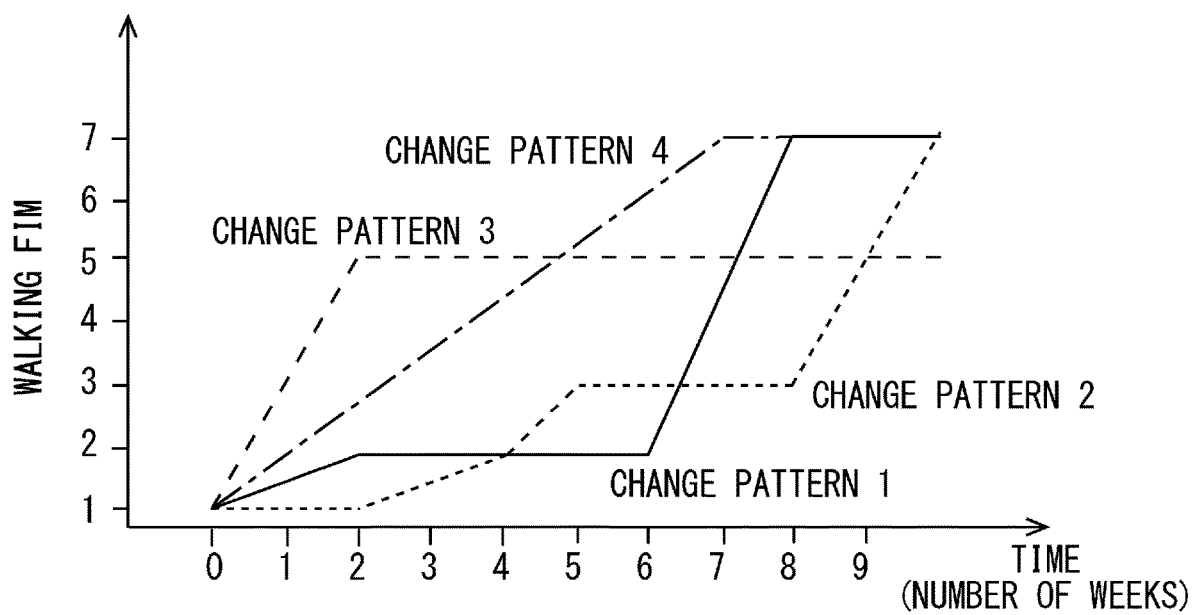
FIG. 7 shows an example of patterns of changes in parameters shown in FIG. 6.
Figure 8:
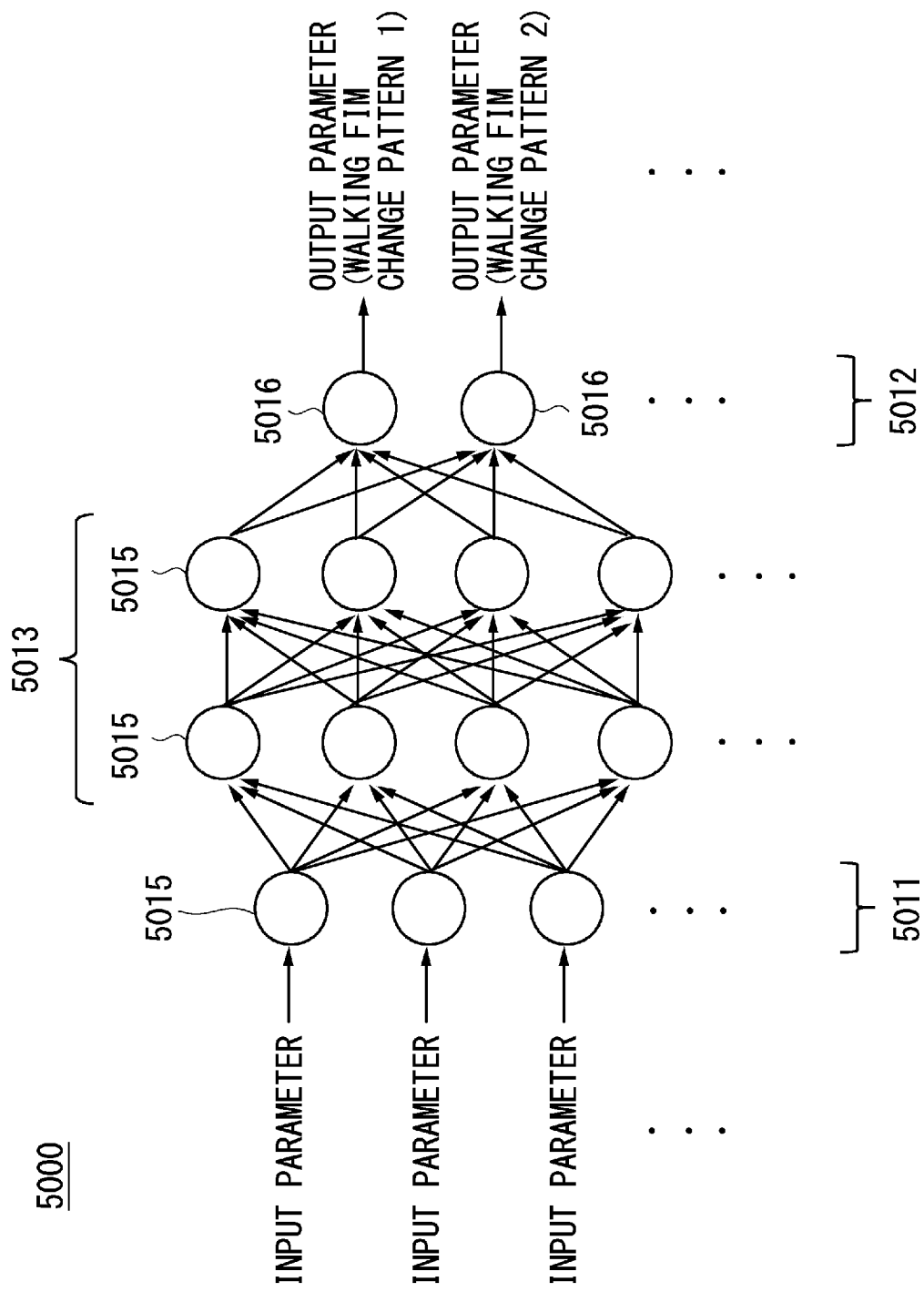
FIG. 8 shows an example of a learning model used in a learning process shown in FIG. 5.
Figure 9:
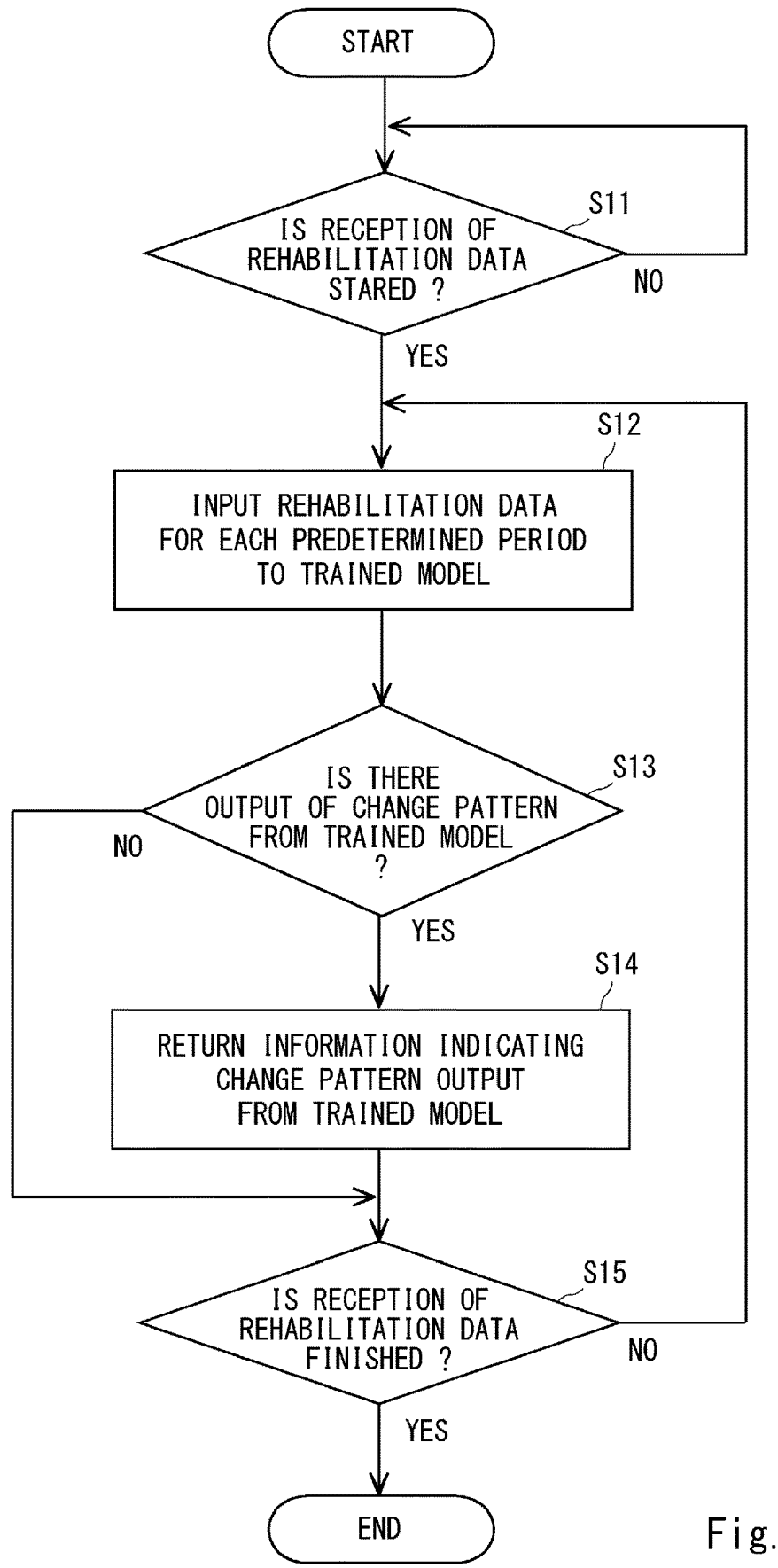
FIG. 9 is a flowchart for explaining an example of a rehabilitation support process performed in the rehabilitation support system shown in FIG. 1.

Next, processes performed in a learning stage (a learning phase) in the control unit 510 of the server 500 will be described with reference to FIGS. 5 and 9. FIG. 5 is a flowchart for explaining an example of a learning process performed by the server 500. FIG. 6 shows a table for explaining a data set for learning used (hereinafter also referred to as a learning data set) in the learning process, and shows an example of parameters that are input to or output from the learning model. FIG. 7 shows an example of patterns of changes in parameters shown in FIG. 6. Further, FIG. 8 shows an example of a learning model used in the above-described learning process.

The server 500 collects rehabilitation data from a plurality of walking training apparatuses 100. Then, the server 500 accumulates the collected rehabilitation data in the data accumulation unit 520. The control unit 510 constructs a trained model from an untrained model by performing pre-processing (preliminary processing) as appropriate on part or all of the information included in rehabilitation data like the one described above and performing machine learning by using the pre-processed data in the learning unit 510b. A pre-processing unit (not shown) disposed in the control unit 510 performs pre-processing (preparatory processing), and the learning unit 510b performs machine learning by using the pre-processed data.

More specifically, the learning unit 510b inputs, for each predetermined period, rehabilitation data about rehabilitation performed by the trainee 900 using the walking training apparatus 100, and thereby generates a trained model for predicting a change in index data. Further, the rehabilitation data input in the above-described process includes at least index data indicating at least one of a symptom, a physical ability, and a degree of recovery of the trainee 900, and training data of the trainee 900 acquired during the rehabilitation in the walking training apparatus 100. Needless to say, since it is in the learning stage, the collected rehabilitation data and the pre-processed data will include data of a plurality of trainees 900.

Basically, the aforementioned predetermined period may be a period in which the time length, the number of times of practices, the number of times of training sessions, or the like is determined in advance. Alternatively, the aforementioned predetermined period may be a period until a value of index data (e.g., a walking FIM) reaches at least an n-level higher level (n is a positive integer), a period until the value reaches at least an n-level lower level, a period until the level changes in either of the directions, or the like. Note that the expression "at least n-levels" is used in the above description because the level could suddenly change by more than n levels such as by n+1 levels. Further, in the case where the rehabilitation data to be pre-processed is not the above-described data on the predetermined-period basis, a process such as a dividing process or a statistical process may be performed as pre-processing so that the rehabilitation data becomes the above-described data on the predetermined-period basis.

Further, the learning unit 510b generates a trained model by performing machine learning by using, as teacher data, data that is obtained in a period until the index data reaches a predetermined target level. That is, the trained model generated in the above-described process is a learning model that predicts (estimates) changes in the index data until the index data reaches the predetermined target level. Needless to say, the predetermined target level may include a plurality of target levels. That is, the generated trained model may be a learning model that predicts changes until the index data reaches a plurality of predetermined target levels. Further, it is also possible to construct a separate trained model for each type of index data. Further, it is also possible to construct a separate trained model for each of the predetermined target levels.

Firstly, as a procedure for generating a trained model like the one described above, a plurality of sets of data for leaning (or data for its pre-processing) are prepared in the data accumulation unit 520 of the server 500. To that end, for example, the control unit 510 accumulates rehabilitation data collected in a certain period as one set of learning data in the data accumulation unit 520. For example, rehabilitation data collected in one walking training session or in one practice of walking training may be prepared as one set of learning data. Note that in the following description, one set of learning data is referred to as a learning data set (also referred to simply as a data set). One data set may include above-described rehabilitation data for each predetermined period or may be rehabilitation data for one predetermined period.

Note that one walking training session is a series of trainings performed by one trainee 900. Further, after one walking training session is completed by the trainee 900, the next trainee 900 performs training in the same walking training apparatus 100. One walking training session usually takes about 20 to 60 minutes. One practice of walking training is one unit during which the trainee 900 continuously walks, included in one walking training session. One walking training session includes a plurality of walking training practices. For example, one practice takes about five minutes. Specifically, in one walking training session, the trainee 900 takes a five-minute break after every time he/she performs walking training for five minutes. That is, a walking training practice and a break are alternately repeated in one walking training session. The five-minute interval between breaks is the time for one practice. Needless to say, neither of the time for one training session and the time for one practice is limited to any particular time period. That is, they may be set as appropriate for each trainee 900.

Further, rehabilitation data collected in a period shorter than the period of one practice may be prepared as one data set, or rehabilitation data collected in a period longer than the period of one practice may be prepared as one data set. Further, data obtained in a period before the training staff member 901 gives an encouraging talk or changes a setting parameter may be prepared as one data set. Further, data obtained in a period until a certain value of index data changes m times (m is a positive integer) may be prepared as one data set.

Then, the pre-processing unit (not shown) of the control unit 510 performs, if necessary, pre-processing for the rehabilitation data prepared as described above, stores the pre-processed rehabilitation data in the data accumulation unit 520, and reads out rehabilitation data for each predetermined period stored in the data accumulation unit 520 (step S1).

The processes from the reading to the inputting to the untrained model described above may be performed on a dataset-by-dataset basis. Although one data set may include only one rehabilitation data for a predetermined period as described above, one data set preferably includes a plurality of rehabilitation data. When one data set includes a plurality of rehabilitation data, they may be data that is obtained by dividing a series of rehabilitation data for training performed by a certain trainee 900 (possibly for training performed by a certain trainee 900 with assistance by a certain training staff member 901) into data for each predetermined period.

An example of the data set is described with reference to FIG. 6. FIG. 6 is a table for explaining the data set. As described above, one data set includes rehabilitation data including at least index data and training data. In the example shown in FIG. 6, a setting parameter, detection data, trainee data, staff data, a walking FIM at the present time (a current walking FIM), and a pattern of changes in the walking FIM are associated with each other and constitute one data set. Each of these various data constituting one data set is a value for each predetermined period. When the value is not uniquely determined, it can be a statistical value such as a representative value or an average value that is obtained as a result of a statistical process over the predetermined period.

The setting parameter and the detection data are examples of the training data. Note that the trainee data may be data of a trainee that includes no index data, or may include index data. The trainee data and the staff data are included in the data set because these information items may also affect the result. The current walking FIM is an example of the index data. Even an initial walking FIM at a stage at which training has not been performed yet can be used as the current walking FIM. Needless to say, a value other than the walking FIM can be used, or a plurality of types of index data can be used.

The pattern of changes in the walking FIM is a pattern indicating how the walking FIM has changed in one data set of interest included as a correct-answer label, and values shown here are values for specifying the type of the pattern of changes.

Specific examples of the four patterns of changes in the walking FIM shown in FIG. 6 include, for example, patterns of changes (hereinafter also referred to as change patterns) shown in FIG. 7. A change pattern 1 shown in FIG. 7 is a pattern in which the value sharply increases near the middle on the time axis from a stagnation period in the first half and enters a stagnation period again in the second half. A change pattern 2 shown in FIG. 7 is a pattern in which the value does not significantly changes in the first half and sharply changes in the second half. A change pattern 3 shown in FIG. 7 is a pattern in which the value sharply changes in the first half but does not reach the maximum value of the walking FIM ("7" in this example). A change pattern 4 shown in FIG. 7 is a pattern in which the value changes at a constant rate before the vicinity of the middle on the time axis and enters a stagnation period at the maximum value in the second half.

For example, when the predetermined target level for the walking FIM is set to "5", any of the change patterns 1 to 4 shown in FIG. 7 can be used as a correct-answer label of the teacher data. For example, when the predetermined target level for the walking FIM is set to "7", all of the change patterns 1, 2 and 4 shown in FIG. 7 can be used as a correct-answer label of the teacher data, but the change pattern 3 cannot be used as the correct-answer label. However, even in this case, in reality, the waling FIM may not reach a target level such as the change pattern 3, so it is desirable to use the change pattern 3 as a correct-answer label. Only the patterns over several weeks are shown in FIG. 7. However, in consideration of infinite weeks, such use is possible That is, even when the predetermined target level for the walking FIM is set to "7", it is possible to interpret that the change pattern 3 represents only a part of the process for eventually reaching the target level. Therefore, the change pattern 3 can be used as a correct-answer label.

Each of the values of the correct-answer labels can be associated with a respective one of the output parameters (a respective one of the output nodes) of the untrained model. In reality, training may change along various recovery curves depending on the trainee 900. Therefore, the change pattern does not necessarily have to be accurate. For example, a plurality of types of change patterns may be determined by a person who makes the data set, and he/she can determine the closest change pattern among them as a correct-answer label for one data set of interest. Needless to say, the correct-answer label may be a pattern of changes of other types of index data, or a pattern of changes of a combination of a plurality of types of index data. Further, the correct-answer label is not limited to the change patterns. That is, the correct-answer label may be any label that indicates a change in index data, such as a simple final result of one or a plurality of types of index data.

Note that in FIG. 6, for simplifying the explanation, each of the setting parameter, the detection data, the trainee data, the staff data, and the current walking FIM is shown as one data (e.g., parameter_1). However, as described above for the current walking FIM, in reality, each of the setting parameters, the detection data, the trainee data, the staff data, and the current walking FIM may have a plurality of data. For example, the setting parameter may include two or more data such as a partial weight-supported amount, vertical positions of the handrails 130*a*, and the like. The detection data may include detection data obtained from a plurality of sensors. The trainee data may include two or more data such as a gender and an age of the trainee 900. The staff data may include two or more data such as an age and a gender of the training staff member 901 as described above.

Further, as described above, when the data set includes the detection data, it is not limited to raw detection data and may include data that is obtained by performing a predetermined process on detection data. For example, a feature value extracted from detection data acquired in a certain period may be used as learning data. For example, the data set may include a maximum value, a minimum value, a local maximum value, a local minimum value, an average value, etc. of detection data obtained in one practice. The control unit 510 may calculate a feature value from the detection data accumulated in the data accumulation unit 520. Alternatively, feature values may be accumulated in the data accumulation unit 520. The data accumulation unit 520 may accumulate raw data of detection data and the learning model may include a layer in which a feature value is calculated.

Note that there is a possibility that when one data set is generated, either or both of the index data and the training data is not included in the rehabilitation data from which the one data set is generated. However, information that is not included in the rehabilitation data may be regarded as information indicating the same value as that of the immediately preceding information and the same value may be included in the rehabilitation data. Further, the rehabilitation data may be data about rehabilitation that is performed by the trainee 900 using the walking training apparatus 100 while being assisted by the training staff member 901 as required. Therefore, an example of a data set including staff data and trainee data has been shown. This is because the index data may change according to the assistance (including communication) and/or according to the feature of the trainee.

Next, the pre-processing unit selects, as the teacher data, rehabilitation data obtained in a period until the index data reaches the predetermined target level from among the read data sets (rehabilitation data for each predetermined period) (step S2). In the step S2, a plurality of data sets are selected as teacher data from among the plurality of data sets stored in the data accumulation unit 520. However, in the step S2, among the rehabilitation data for a plurality of predetermined periods included in one data set selected in this process, rehabilitation data that are obtained in periods after the index data reaches the predetermined target level can be excluded from the teacher data. Note that the data set shown in FIG. 6 has been regarded as an example of data for which the process in the step S1 has already been performed. Alternatively, it can also be regarded as an example of data for which the process in the step S2 has already been performed.

Then, the learning unit 510b inputs the teacher data prepared as described above to the untrained model and thereby generates (constructs) a trained model (step S3). As shown in FIG. 6, the input parameter to the untrained model includes the index data and the training data, and the output parameter from the untrained model can be a pattern of changes of the index data (a pattern indicating changes in the index data) as shown as the change pattern of the walking FIM (hereinafter also referred to as the walking FIM change pattern).

For example, as shown in FIG. 8, the learning unit 510b can construct a learning model by a neural network in which an intermediate layer (also known as a hidden layer) 5013 is provided between an input layer 5011 and an output layer 5012. The input layer 5011 includes a plurality of nodes 5015 and inputs each data included in the data set. The output layer 5012 includes a plurality of output nodes 5016 and outputs, as an output parameter of each output node 5016, a value referred to as a certainty factor or the like of each walking FIM change pattern. The intermediate layer 5013 includes a plurality of nodes 5015. Each node has an activation function. A weight is assigned to an edge that connects nodes with one another. A learning model 5000 may be a model in which index data, training data, and the like are used as explanatory variables, and the change pattern of the walking FIM is used as an objective variable. Needless to say, for example, the learning model may further include a final output layer that outputs a node number (i.e., corresponding to a pattern number) of a node having the highest certainty factor among the output nodes 5016 in FIG. 8.

Note that the type of the untrained model to be trained by the learning unit 510b and its algorithm are not limited to any particular types and algorithms. However, a neural network can be used as the algorithm. In particular, as shown in FIG. 8, a deep neural network (DNN) using multiple intermediate layers 5013 may be used. As the DNN, for example, a feedforward (forward propagation type) neural network such as a multilayer perceptron (MLP) employing an error back propagation method can be used.

When the learning unit 510b generates the trained model, it inputs each of a plurality of sets of teacher data to the untrained model an appropriate number of times. For example, the learning unit 510b generates a trained model by using some of the sets of teacher data (training data for leaning) and checks the accuracy of the generated trained model by using the remaining sets as test data. As a result of the checking, if the accuracy is satisfactory, it is implemented as it is. On the other hand, if the accuracy is poor, some process, such as changing the pre-processing or performing tuning, is performed and then the trained model is generated and evaluated again. Note that it is also possible to prepare both evaluation data for checking the accuracy and test data for testing the final accuracy in advance. Further, it is possible to generate, according to the item of the data set that is input when the trained model is generated, the trained model in which that item is taken into consideration.

Further, hyper parameters to be tuned are not limited to any particular parameters. Examples of the hyper parameters to be tuned include the number of layers of the neural network, the number of units (number of nodes) in each layer, the number of times of iterative learning using the same data set (number of epochs), and the number of input data to be passed to the model at a time (a batch size). Further, examples of the hyper parameters to be tuned include a learning coefficient and a type of an activation function. Note that the learning coefficient is also referred to as a learning rate and may be as a value for determining how much the weight of each layer is changed at a time.

Further, some of the rehabilitation data may be input as image data to a feature extraction unit including, for example, a convolution layer and a pooling layer in a CNN (Convolutional Neural Network). Examples of the image data include image data that is obtained by photographing the trainee 900 so that his/her posture can be recognized. In such a case where the feature extraction unit is provided, a result of extraction of features from the image data may be input to all the connection layers in parallel with other input parameters.

By the above-described process, it is possible to generate a learning model capable of predicting a change in index data of a trainee 900 when the trainee 900 performs rehabilitation by using the walking training apparatus 100. The control unit 510 writes the constructed trained model (e.g., a learning model 5000) into the model storage unit 521. Note that as described above, it is possible to construct a trained model for each type of index data or each target level, and in such a case, a plurality of trained models are stored in the model storage unit 521.

In this way, as will be described later for the operation stage, in the walking training apparatus 100 using the trained model, it is possible to successively input data acquired during the rehabilitation to the model as input parameters and thereby to show predicted change in the index data. Therefore, the training staff member 901 can assist the trainee 900 (i.e., give rehabilitation support) such as changing a setting parameter by effectively using the shown information.

Further, as described above, the training data may include a setting parameter in the walking training apparatus 100 at the time when the trainee 900 performs the rehabilitation. In this way, it is possible to construct a learning model so that it can predict the change in the index data while taking the setting parameter into consideration.

Further, as described above, the rehabilitation data can include trainee data indicating a feature(s) of the trainee 900. Note that examples of the features of the trainee 900 include a height, a weight, a gender, a disease, and a symptom, and the trainee data may include physical information indicating such features. In this way, it is possible to construct a learning model so that it can predict the change in the index data while taking the feature of the trainee 900 into consideration. In particular, the trainee data may include symptom data indicating at least one of a disease(s) (a name(s) of a disease(s) or a disorder(s)) and a symptom(s) of the trainee 900. This is because it is expected that the prediction result changes according to the disease or the symptom of the trainee 900. The symptom data is data in which the above-described symptom information is described. In particular, in the case of walking training, examples of symptoms that are included in the symptom data include a trunk backward movement, a trunk forward bending, a trunk diseased-side movement, a knee joint flexion, difficulty of the toe-off, difficulty in keeping the swinging leg, a trunk backward bending, a pelvic retreat, a lower leg forward bending, a knee joint extension, a flexed knee joint, and swinging. Further, examples of the symptoms that are included in the symptom data include a trunk normal-side movement, vaulting, pelvic elevation, hip joint external rotation, circumduction, and a medial whip.

Further, the rehabilitation data may also include, in addition to the feature (or as a concept that is included in the feature) of the trainee 900, data indicating a preference(s) of the trainee 900 entered in the walking training device 100.

Further, as described above, the trained model generated by the learning unit 510*b* may be a model for predicting a pattern of changes in the index data in which the index data gets closer to the predetermined target level. In this way, it is possible to construct a learning model capable of outputting a pattern of changes.

Further, the control unit 510 may further include an extraction unit that extracts, from rehabilitation data of a plurality of trainees, rehabilitation data of a trainee whose condition indicated by the index data at an early stage of the training (i.e., initial data) is at a predetermined level (i.e., is a predetermined state). This extraction unit can be formed as a part of the pre-processing unit or included in the learning unit 510*b*, and can be configured, for example, to perform a process such as stratification according to the initial symptom. By storing the extracted resultant rehabilitation data in the data accumulation unit 520, it can be read at the time of the learning.

Further, the learning unit 510*b* generates a trained model for the above-described trainee at the predetermined level by using the data set for the rehabilitation data extracted by the extracting unit as an input. In this way, it is possible to construct a trained model so that it can predict changes in the index data for the above-described trainee whose index data at the early stage of the training is at the predetermined level.

Further, the above-described extraction unit may be configured to extract rehabilitation data of the following trainee 900. That is, this trainee 900 means a trainee 900 of which a combination of index data at an early stage of the training and index data at the time when it is at the predetermined level (i.e., index data at a stage at which rehabilitation data is extracted, such as index data at the current stage) is a predetermined combination. In this way, it is possible to construct a trained model so that it can predict changes in index data for a trainee of which the index data at the early stage of the training and the index data at the current stage constitute a predetermined combination.

Operation Stage: Use of Learning Model

Next, processes performed in the operation stage (the inference phase) in the walking training apparatus 100 and the server 500 will be described. As described above, the walking training apparatus 100 is configured so as to be able to access a trained model, so that it can use the trained model. Note that the trained model may also be referred to as a trained module. In the operation stage, in general, the walking training apparatus 100 and the server 500 connected thereto cooperate with each other. That is, they serve as a rehabilitation support system and perform a rehabilitation support process.

In order to operate the above-described trained model, the walking training apparatus 100 mainly includes a prediction acquisition unit and a presentation unit as described below, and the server 500 may include a prediction unit 510*a* and a model storage unit 521 in which the trained model is stored. The prediction acquisition unit may include, for example, an input/output control unit 210*c* and an input/output unit 231. The presentation unit may include a notification control unit 210*d*, and may also include the display control unit 213, the management monitor 139, the training monitor 138, an audio control unit and a speaker(s) (not shown), and so on.

The prediction acquisition unit of the walking training apparatus 100 acquires, as an input parameter, rehabilitation data including at least training data and index data of the trainee 900 who performs the training (who starts or is performing the training). The training data acquired in this process may include past data at this point in time, or may include only the existing information such as setting parameters at this point in time. Further, the index data acquired in this process may include at least current index data such as the current walking FIM, or may include past index data instead of or in addition to the current index data.

Then, the prediction acquisition unit can transmit the acquired rehabilitation data to the server 500, make the server 500 predict a change in the index data, and obtain information indicating a result of the prediction returned from the server 500.

This prediction can be made mainly by the prediction unit 510*a* of the server 500. The prediction unit 510*a* inputs rehabilitation data including at least the index data and the training data of the trainee 900 who starts or is performing the training to the trained model, and predicts a change in the index data.

Therefore, the prediction unit 510*a* inputs rehabilitation data to the trained model stored in the model storage unit 521 through the response processing unit 510*c*, operates the trained model, and inputs a necessary part of the rehabilitation data or the whole rehabilitation data to the trained model as an input parameter(s). It is assumed that the rehabilitation data input to the trained model has been pre-processed in advance by the pre-processing unit or the prediction acquisition unit of the control unit 510 as required so that the rehabilitation data becomes rehabilitation data for each predetermined period. The prediction unit 510*a* receives a value (e.g., a certainty factor) of each output parameter output from the trained model in response to such an input, and outputs, as a prediction result, a result indicating a pattern that is predicted as a walking FIM change pattern having the highest certainty factor among them. The prediction unit 510*a* transmits this prediction result to the walking training apparatus 100 through the response processing unit 510*c*. Note that the response processing unit 510*c* communicates with the walking training apparatus 100 through the communication IF 514.

The prediction acquisition unit of the walking training apparatus 100 receives the prediction result output from the prediction unit 510*a* from the server 500 side. The presentation unit of the walking training apparatus 100 presents (i.e., shows) the prediction result (e.g., the predicted change in the index data such as the walking FIM change pattern having the highest certainty factor) obtained by the prediction acquisition unit. This presentation can be performed by, for example, displaying the prediction result in the form an image on the management monitor 139 or outputting it in the form of a voice or a sound from the speaker(s).

In this way, the training staff member 901 who assists a trainee 900 can give rehabilitation support while checking the prediction result of the index data of the trainee 900 when he/she performs the rehabilitation using the walking training apparatus 100.

Figure 10:
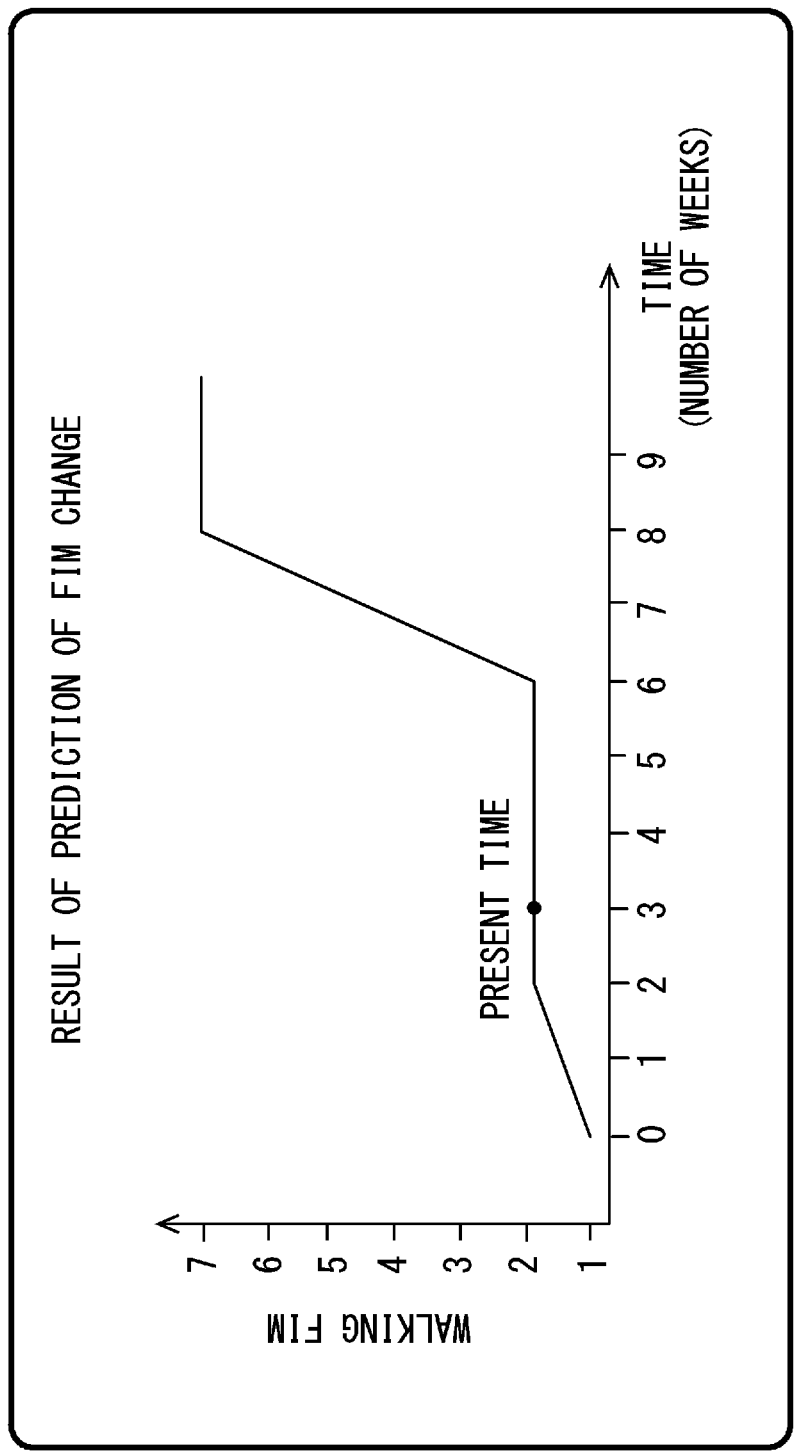
FIG. 10 shows an example of an image presented to a training staff member in the rehabilitation support process shown in FIG. 9.

An example of the rehabilitation support process performed in the rehabilitation system including the walking training apparatus 100 and the server 500 will be described with reference to FIGS. 9 and 10 and the like. FIG. 9 is a flowchart for explaining an example of the rehabilitation support process performed in the server 500. FIG. 10 shows an example of an image presented (i.e., shown) to the training staff member 901 in the rehabilitation support process shown in FIG. 9.

Firstly, the input/output control unit 210*c* of the walking training apparatus 100 outputs acquired rehabilitation data that could serve as an input parameter to the server 500 through the input/output unit 231. When the response processing unit 510*c* of the server 500 receives this data through the communication IF 514 (Yes at step S11), it starts a response process. The response processing unit 510*c* passes the received data to the prediction unit 510*a*. Note that in the case where rehabilitation data that is not data for each predetermined period is received, the response processing unit 510*c* passes the received data to a pre-processing unit (not shown), and the pre-processing unit converts the passed data into data for each predetermined period and passes the obtained data to the prediction unit 510*a*. The prediction unit 510*a* analyzes the data for each predetermined period, divides it into a plurality of item data, and outputs each of the item data as a respective one of input parameters in the input layer in the trained model stored in the model storage unit 521 (step S12).

The prediction unit 510*a* performs calculation by operating the trained model and determines whether or not there is an output that is predicted as a change pattern (in this example, a walking FIM change pattern) by determining (i.e., examining) each output parameter from the output layer (step S13). Further, the determination of the output parameters can be made by performing a process by using thresholds each of which is prepared for a respective one of the values of the output parameters in advance (or by using a common threshold). The threshold corresponds to a predetermined certainty factor and the predetermined certainty factor can be changed according to the change pattern. Needless to say, in the case of a model whose output parameter can have only two values, i.e., values 0 and 1, all that has to be performed is to determine whether the output parameter is 0 or 1.

In the case of Yes at the step S13, for example, when a certain output parameter exceeds the predetermined certainty factor, the prediction unit 510*a* passes information indicating a walking FIM change pattern corresponding to the output parameter, which exceeds the predetermined certainty factor, to the response processing unit 510*c*. Then, the response processing unit 510*c* returns this information to the walking training apparatus 100 side through the communication IF 514 (step S14). The returned information may be a command to the walking training apparatus 100. In the case of No at the step S13, the prediction unit 510*a* proceeds to a step S15 (which will be described later) without going through the step S14.

As described above, in the steps S13 and S14, the prediction unit 510*a* performs calculation by operating the trained model, and the response processing unit 510*c* generates, for a walking FIM change pattern(s) corresponding to an output parameter(s) output as certainty factor(s) higher than the threshold among the output parameters from the output layer, a command corresponding to the output parameter(s). Meanwhile, the prediction unit 510*a* does not perform any particular process for the other output parameters. That is, in some cases, the response processing unit 510*c* does not output any command at all depending on the calculation result. Note that the command can be generated by, for example, having the response processing unit 510*c* read (i.e., select) a command corresponding to the output parameter (corresponding to the output node) from a group of commands stored in advance. Each of the output parameters (each of the output nodes) of the trained model may be associated with a command in advance. Further, the command may simply indicate information indicating the output parameter (e.g., information indicating the ordinal position of the node in the output layer), as long as the command can be interpreted on the walking training apparatus 100 side. The response processing unit 510*c* transmits the generated command to the walking training apparatus 100 side through the communication IF 514.

After the process in the step S14, the response processing unit 510*c* determines whether or not the reception of the rehabilitation data has been completed (step S15). Then, when the reception has been completed, the response processing unit 510*c* finishes the process, whereas when the reception has not been completed, it determines that the rehabilitation is in progress and returns to the step S12.

In the walking training apparatus 100, the input/output control unit 210*c* receives the command transmitted in the step S14 and passes the received command to the notification control unit 210*d*. The notification control unit 210*d* performs notification control corresponding to this command for the display control unit 213 or an audio control unit (not shown). Notification controls each of which corresponds to a respective one of the commands in the command group that could be transmitted from the server 500 side may be stored in the notification control unit 210*d* in advance.

For example, the notification control unit 210*d* makes the display control unit 213 output, to the management monitor 139, a display control signal for displaying, for example, an image corresponding to the command on the management monitor 139. For example, the notification control unit 210*d* can display a GUI (Graphical User Interface) image shown in FIG. 10 on the management monitor 139.

The GUI image 139*a* is an image that is displayed on the management monitor 139 or superimposed thereon as a pop-up image. The GUI image 139*a* may include a graph showing changes in the walking FIM over time (over elapsed weeks), and indicate the current walking FIM and the current time (the number of weeks) as shown in FIG. 10. Note that although an example in which only the walking FIM is predicted is described here, the same applies to other index data. Further, when a plurality of types of index data are simultaneously predicted, they may be simultaneously shown, for example, in the same graph or in different graphs.

Further, the notification control unit 210*d* may make the aforementioned audio control unit output an audio control signal for outputting a voice or a sound corresponding to the command to a speaker(s) so that the voice or the sound is output from the speaker(s). However, the aforementioned speaker(s) may be, for example, a wireless earphone(s) (e.g., a bone-conduction-type earphone(s)) attached to an ear(s) or the like of the training staff member 901 in order to prevent the trainee 900 from hearing the sound or the voice. Needless to say, the notification control unit 210*d* may be configured so as to output a voice or a sound in addition to displaying an image.

By the above-described process, the training staff member 901 who assists a trainee 900 can give rehabilitation support while checking predicted changes in the index data when he/she performs the rehabilitation using the walking training apparatus 100. For example, it is possible to predict a stagnation state (a plateau) in which the rise of the index data temporarily stagnates even though the training is continued, so that the training staff member 901 can make a determination as to, for example, whether or not to quit the training halfway therethrough or whether or not to change the setting parameter. Further, since the trained model exists in the server 500, a plurality of walking training apparatuses 100 can be operated by using the common trained model.

In the above description, an example in which the prediction acquisition unit of the walking training apparatus 100 obtains a prediction result by using the prediction unit 510*a* is shown. Since this prediction acquisition unit is a part that obtains a prediction result, it may also be referred to as a prediction unit. However, the walking training apparatus 100 may just acquire rehabilitation data that is used as an input parameter, transmit the acquired rehabilitation data to the server 500 side, and wait for a reply therefrom. Meanwhile, the prediction unit 510*a* on the server 500 side may make a prediction on its own.

Further, the walking training apparatus 100 may also be configured so as to be able to access a trained model that is created for each state indicated by initial data by using the above-described extraction unit. In this example, these trained models may be stored in the model storage unit 521. In this case, the walking training apparatus 100 may further include a designation unit described below. This designation unit designates a trainee 900 by using, for example, initial index data or a name associated with the initial index data. This designation unit can have a GUI image that is displayed on the management monitor 139 and receives such designation.

The prediction acquisition unit inputs rehabilitation data including at least training data of the trainee 900 designated by the designation unit to a trained model corresponding to the index data of the trainee 900 designated by the designation unit, and predicts a change in the index data and obtains a result of the prediction. The obtained result becomes a result for a trainee at a predetermined level suitable for the trainee 900. The presentation unit shows a predicted change in the index data acquired by the prediction acquisition unit.

By the above-described process, the training staff member 901 who assists a trainee 900 can give rehabilitation support while checking a change in the index data predicted for a trainee whose index data at the early stage of the training is at a predetermined level when the trainee 900 performs the rehabilitation using the walking training apparatus 100.

Further, in the case where a separate trained model is constructed for each type of the index data, the walking training apparatus 100 can be configured so as to be able to access these trained models. In this case, the walking training apparatus 100 may include a type designation unit that designates a type of index data to be predicted. This type designation unit may have basically the same configuration as that of the above-described designation unit except that an object to be designated is different from that in the designation unit. Further, similarly, the presentation unit can show a predicted change in the index data that the prediction acquisition unit has acquired from the trained model that predicts the index data of the designated type.

In the case where a separate trained model is constructed for each predetermined target level, the walking training apparatus 100 can be configured so as to be able to access these trained models. In this case, the walking training apparatus 100 may include a level designation unit that designates a predetermined target level to be predicted. This level designation unit may have basically the same configuration as that of the above-described designation unit except that an object to be designated is different from that in the designation unit. Further, similarly, the presentation unit can show a predicted change in the index data that the prediction acquisition unit has acquired from the trained model that predicts the index data obtained in a period until the index data reached the designated predetermined target level. Further, although it is not described, the same applies to the case where a different trained model is constructed for, for example, every combination of each type of index data and each predetermined target level.

Effect

As described above, according to this embodiment, it is possible to generate a trained model capable of predicting a change in index data of a trainee 900 when the trainee 900 performs rehabilitation by using the walking training apparatus 100. Further, according to the walking training apparatus 100 in accordance with this embodiment, since the walking training apparatus 100 can access the trained model generated as described above, the training staff member 901 can give rehabilitation support while checking a result of a prediction of index data of a trainee 900 by using the trained model. In this way, the training staff member 901 can reduce the loss of opportunities for the trainee 900, such as making the trainee 900 terminate the training at an optimal timing.

Supplemental Remarks on Method and Program

As can be understood from the above-described description, in this embodiment, it is also possible to provide a learning method including a learning step described below. In the learning step, a learning model for predicting a change in index data indicating at least one of the symptom, the physical ability, and the degree of recovery of a trainee 900 is generated by inputting rehabilitation data, for each predetermined period, about rehabilitation performed by the trainee 900 using the walking training device 100 to the model. As described above, this rehabilitation data includes at least index data and training data of the trainee 900 acquired during the rehabilitation in the walking training apparatus 100. Further, in the learning step, the learning model is generated by using, as teacher data, data obtained in a period until the index data reaches a predetermined target level.

In this embodiment, as can be understood from the above-described description, it is also possible to provide a method for supporting rehabilitation (a method for operating the walking training apparatus 100) in the walking training apparatus 100 capable of accessing a trained model, which is a learning model trained by the above-described learning method. Further, this method includes the below-shown prediction step and the presentation step. In the prediction step, rehabilitation data including at least index data and training data of the trainee 900 performing the training is input to the trained model, and a change in the index data is predicted. In the presentation step, the change in the index data predicted in the prediction step is shown.

In this embodiment, as can be understood from the above-described description, it is also possible to provide a program (a learning program) for causing a computer to perform the above-described learning step. Further, needless to say, it is also possible to provide a trained model trained by the learning apparatus, a trained model trained by the learning method, and a trained model trained by the learning program. Further, in this embodiment, as can be understood from the above-described description, it is also possible to provide a rehabilitation support program for causing a computer of the walking training apparatus 100 capable of accessing the above-described trained model to execute the above-described prediction step and presentation step.

Second Embodiment

Differences of a second embodiment from the first embodiment will be described together with their effects. Further, although it is not specifically described, the various examples described above in the first embodiment can also be applied to this embodiment.

In a learning apparatus according to this embodiment, as pre-processing, rehabilitation data is divided for each of periods from the start of the training, and a trained model is generated from the divided rehabilitation data. Then, in the walking training apparatus 100 according to this embodiment, a prediction is made by using the trained model trained as described above.

In a learning stage, the learning unit 510b inputs rehabilitation data for each predetermined period to an untrained model, and generates a trained model that predicts changes in index data over a predetermined period longer than the aforementioned predetermined period (e.g., the aforementioned predetermined period×N) (hereinafter referred to as the other predetermined period). Note that N is an integer equal to or greater than two. Therefore, the learning unit 510b generates a trained model by using, as teacher data, rehabilitation data obtained over the other predetermined period (or rehabilitation data including at least such rehabilitation data).

For example, a plurality of types of rehabilitation data, such as from the start of the training to the second week and from the start of the training to the fourth week, are prepared. Then, a different trained model is constructed by using only a respective one of the plurality of types of rehabilitation data. When a trained model for any of the types is constructed, the rehabilitation data input as the teacher data is data that is obtained in a period until the index data reaches a predetermined target level. That is, the difference from the first embodiment is that the rehabilitation data is data over the aforementioned other predetermined period. Therefore, in this embodiment, similarly to the first embodiment, the rehabilitation data input to the untrained model includes index data (including the type of data to be predicted) and training data. Further, for example, in the trained model for the period from the start of the training to the second week, data that is obtained in a period until the index data reaches the predetermined target level among the rehabilitation data in the period from the start of the training to the second week is generated as the teacher data.

In other words, this embodiment corresponds to the first embodiment in which when the trained model is constructed, the rehabilitation data for the respective predetermined periods are input to the untrained model while ignoring rehabilitation data in a period(s) that is not included in the aforementioned other predetermined period.

In this way, in the operation stage, for example, it is possible to predict index data (e.g., a walking FIM) for a period from the start of the training to the fourth week by using the trained model constructed by rehabilitation data in the period from the start of the training to the fourth week, and show the predicted result. This presentation can be performed, for example, only for the value of the index data in the fourth week by a voice or a sound or by an image. However, in this embodiment, it is also possible to show a change pattern over all the weeks including the fourth week as in the case of the GUI image 139a shown in FIG. 10.

Further, as described above, in this embodiment, similarly to the first embodiment, it is possible to input rehabilitation data including index data (including the type of data to be predicted) and training data for each predetermined period to the trained model and thereby to train the trained model. However, the following modification can also be applied. That is, in this embodiment, it is possible to use a correct-answer label so as to generate a trained model in which there is a type of data to be ignored (e.g., a certain setting parameter) in rehabilitation data in the first stage (e.g., in the first two predetermined periods in the aforementioned other predetermined periods).

By operating such a trained model, it is possible to, for example, define three input parameters, and then to predict a change in index data of interest based on two types of data in the first stage such as the first two predetermined periods and predict a change in index data based on the three types of data in the subsequent stages.

Third Embodiment

Figure 11:
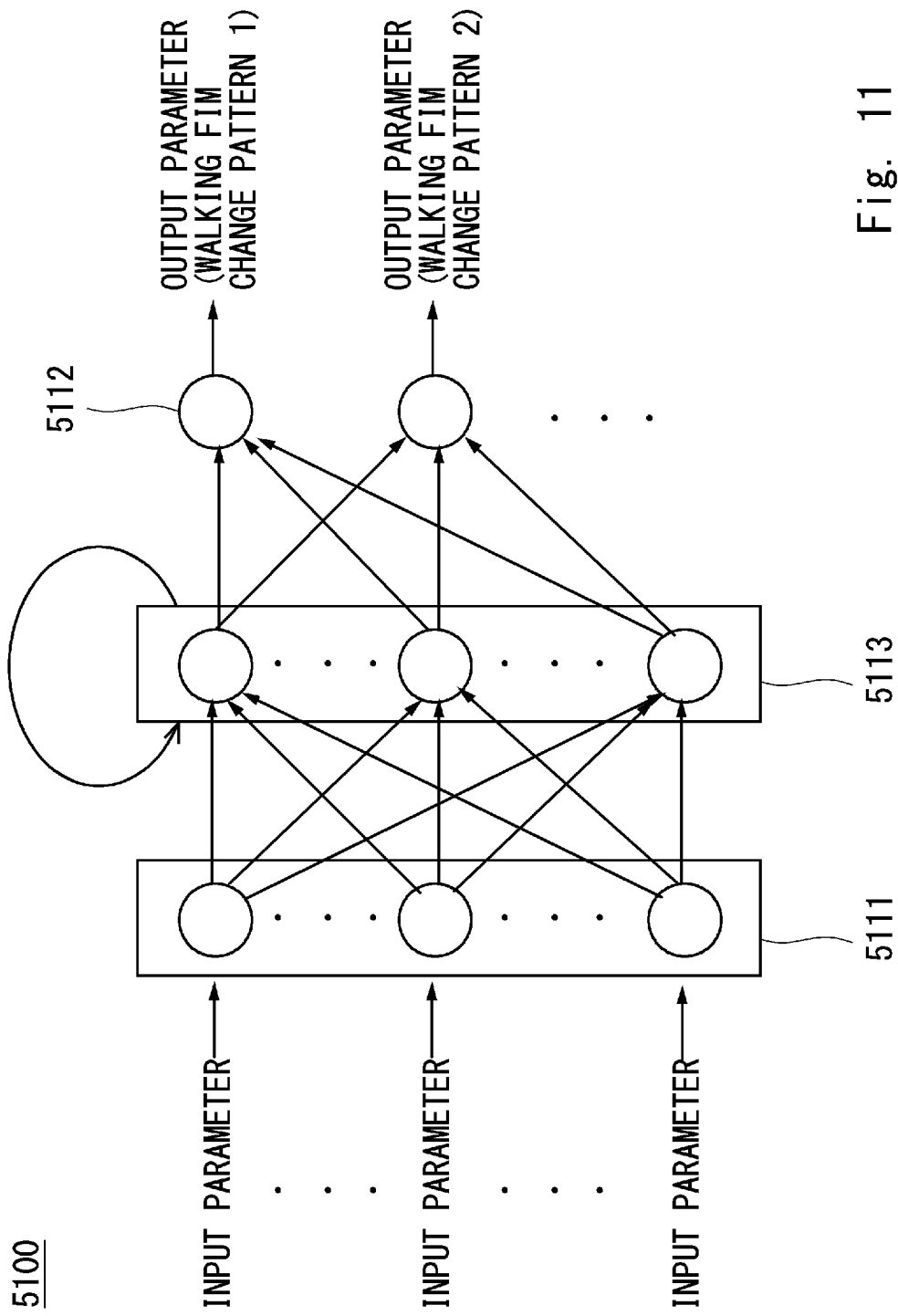
FIG. 11 shows an example of a learning model used in a rehabilitation support system according to a third embodiment.
Figure 12:
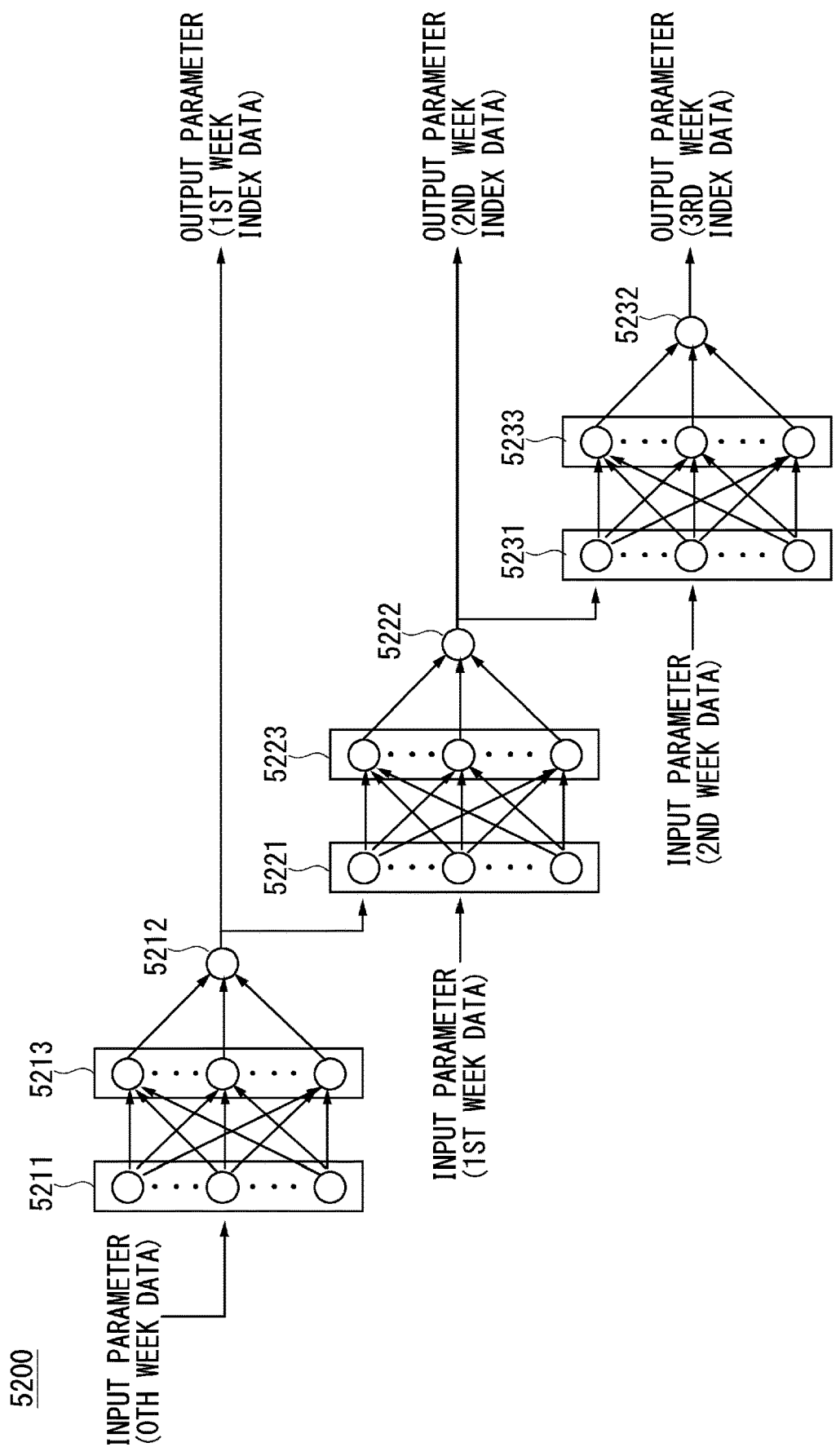
FIG. 12 shows another example of a learning model used in the rehabilitation support system according to the third embodiment.
Figure 13:
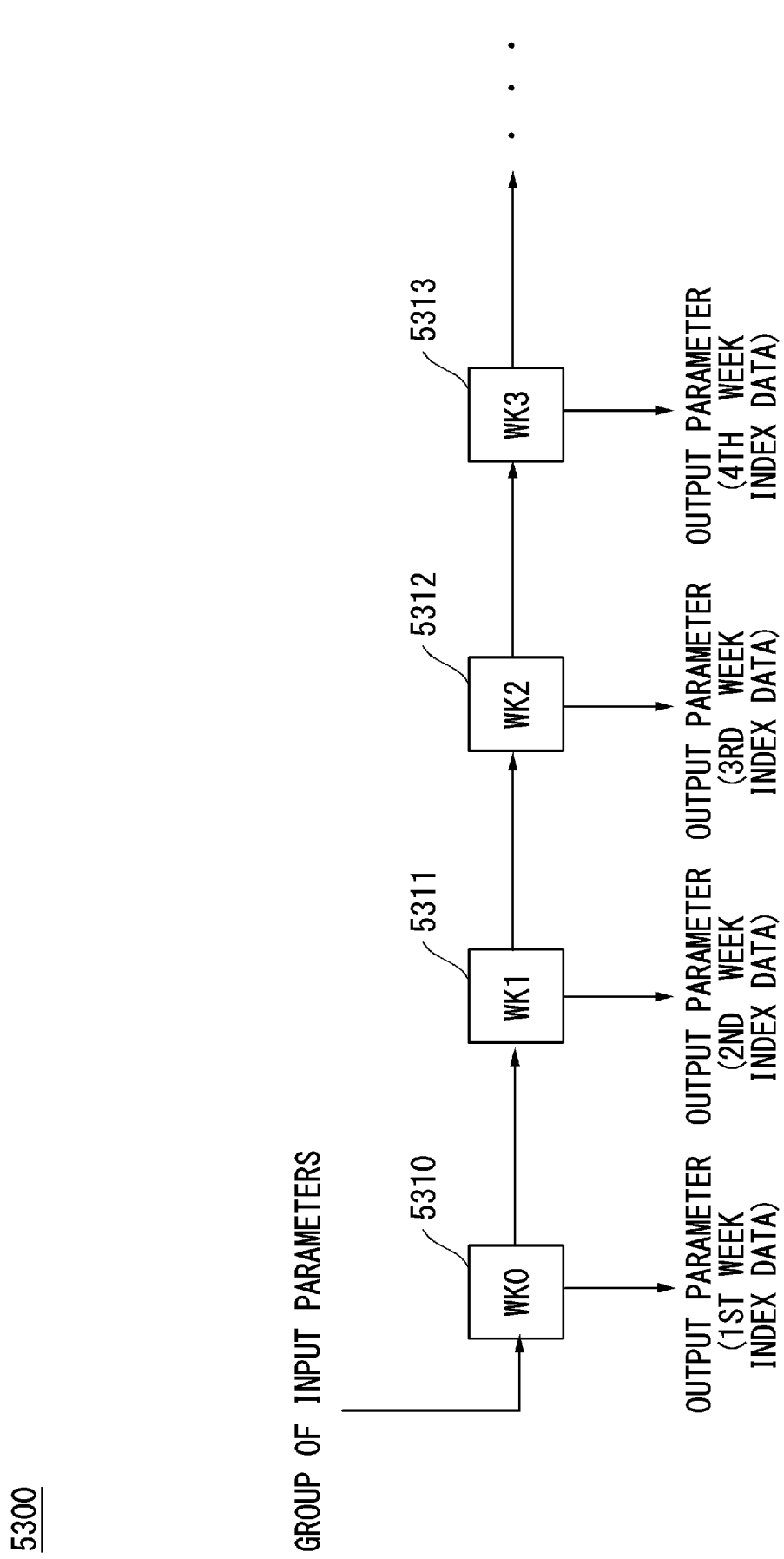
FIG. 13 shows another example of a learning model used in the rehabilitation support system according to the third embodiment.

The third embodiment will be described with reference to FIGS. 11 to 13. FIG. 11 shows an example of a learning model used in a rehabilitation support system according to this embodiment, and both of FIGS. 12 and 13 show other examples of the learning model. In this embodiment, a learning model having an algorithm different from that in the first embodiment is used. Other features and their effects are similar to those of the first embodiment. Further, although it is not specifically described, the various examples described above in the first and second embodiments can also be applied to this embodiment.

Regarding the algorithm used in this embodiment, as the neural network, for example, a neural network having a recursive structure such as an RNN (Recurrent Neural Network) may be used. In this way, it is possible to construct a learning model by a general-purpose algorithm. Further, by using the RNN, it is possible to construct a trained model that outputs, in a timely manner, a change in index data that is predicted from the past only through the period of one data and the period obtained from the number of storage steps based on the current state and a past state that is a little earlier than the current state. Then, it is possible to use such a trained model in the walking training apparatus 100 and thereby to obtain an output for which time-series data is effectively used.

Further, when a recursive model having the RNN is used, for example, one data set may include time-series data so that the learning unit 510b successively inputs rehabilitation data at each time point for each predetermined period. That is, one data set (one learning data set) may include time-series log data. Further, one data set may include feature values extracted from the log data as described above, or may include image data obtained by performing data processing on time-series detection data or the like.

Further, the RNN may be a neural network that is extended to include an LSTM (Long Short-Term Memory) block (also referred to as simply an LSTM). In this way, a gradient vanishing problem in a model including an RNN can be alleviated.

A learning model 5100 shown in FIG. 11 is an RNN including an input layer 5111, an intermediate layer 5113, and an output layer including a plurality of output nodes 5112. Data sets are successively input to the input layer 5111 in a time-series manner. In the learning model 5100, which is the RNN, an output of the intermediate layer 5113 is input to the intermediate layer 5113 again. Similarly to the example shown in FIG. 8, for example, each output node 5112 in the output layer can be associated with a respective one of walking FIM change patterns. Needless to say, it is possible to provide, for example, a final output layer including one output node that outputs a node number having the highest certainty factor among the output nodes 5112 shown in FIG. 11. Note that the node number corresponds to the change pattern number.

Although the change pattern, which is the output parameter in this example, is exemplified by the walking FIM change pattern, the change pattern may be a change pattern of a parameter or data other than the walking FIM and it may include various types of indexes. In the case where one type of index is used, by constructing a learning model 5100 for each type of index, a prediction result for each type can be obtained.

In the operation using the learning model 5100, the walking training apparatus 100 outputs rehabilitation data (without a correct-answer label) similar to that in the learning stage to the server 500, and the prediction unit 510*a* inputs the output rehabilitation data to the learning model 5100 and thereby obtains a prediction result of a change pattern thereof. The response processing unit 510*c* returns a command corresponding to the prediction result to the walking training apparatus 100. The walking training apparatus 100 receives the command from the server 500 and shows the change pattern on, for example, the management monitor 139 as shown in FIG. 10.

A learning model 5200 shown in FIG. 12 is a model in which the learning model 5100 is roughly extended in the time direction, and the aforementioned predetermined period is defined as one week and the output parameter is defined as index data for each week. For example, data in the zeroth week may be defined as data before the training is started, and data in the first week may be defined as data in the period from the start of the training to the first week. Note that the index data, which is the output parameter in this example, may be one of various indexes such as a walking FIM, or may include various types of indexes. In the case where one type of index is used, by constructing a learning model 5200 for each type of index, a prediction result for each type can be obtained.

The learning model 5200 is formed by connecting a first NN including an input layer 5211, an intermediate layer 5213, and an output layer including one output node 5212, and a second NN including an input layer 5221, an intermediate layer 5223, and an output layer including one output node 5222. Further, the learning model 5200 is formed by connecting an additional NN such as a third NN including an input layer 5231, an intermediate layer 5233, and an output layer including one output node 5232.

In the first NN, data in the zeroth week is input to the input layer 5211 as an input parameter, and index data of the first week is output from the output node 5212 as an output parameter. The output node 5212 may be a node that outputs a node number having the highest certainty factor among the nodes 5213. In the 2nd NN, the data in the first week and the output parameter output from the output node 5212 are input to the input layer 5221 as input parameters, and index data of the second week is output from the output node 5222 as an output parameter. The output node 5222 may be a node that outputs a node number having the highest certainty factor among the nodes 5223. The same applies to the subsequent NNs. In the learning model 5200, the number of NNs corresponding to a predetermined number of predetermined periods (weeks in this example) (i.e., the number of predetermined periods included in one data set) or a number obtained by adding one to the predetermined number are provided.

In the learning stage, for example, a trained learning model 5200 can be generated for each NN by performing machine learning by using teacher data like the one described in the first embodiment (teacher data in the week corresponding to the NN) and inputting data in each week to the corresponding NN.

Further, it is also possible to have an LSTM block by, for example, inputting an output of the output node 5212 not only to the input layer 5221 but also to an input layer that is located a predetermined number behind the input layer 5221, such as the input layer 5231 (the same applies to the subsequent output nodes).

In the operation using the learning model 5200, the walking training apparatus 100 outputs rehabilitation data (without a correct-answer label) similar to that in the learning stage to the server 500, and the prediction unit 510*a*, for example, divides the output rehabilitation data into data for each week, inputs the divided data to the learning model 5200, and thereby obtains a prediction result. The prediction unit 510*a* summarizes the values of all the output parameters and arranges the summarized values into data by which, for example, a change pattern like the one shown in FIG. 10 can be drawn, and the response processing unit 510*c* returns a command corresponding to the arranged data to the walking training apparatus 100. The walking training apparatus 100 receives the command and shows the change pattern on, for example, the management monitor 139 as shown in FIG. 10.

A learning model 5300 shown in FIG. 13 may be a model in which auto-encoders 5310, 5311, 5312, 5313, . . . , each of which includes, in an intermediate layer, the number of nodes equal to the number of dimensions into which the input data is to be compressed are arranged for each week. Note that similarly to the example shown in FIG. 12, the predetermined period is one week in this example.

Each of the auto-encoders 5310 and the like arranged in the learning model 5300 may be a three-layer perceptron composed of three layers, i.e., composed of an input layer, an intermediate layer, and an output layer. Further, an output of the intermediate layer is externally output as an output parameter. Although not shown in FIG. 13, in each of the auto-encoders 5310 and the like, the output layer is configured so that output parameters that reproduce all the input parameters input from the input layer are output, and all or some of the output parameters are input to the input layer in the subsequent stage. In each of the auto-encoder 5310 and the like, the number of output layers in the preceding stage may be equal to the number of input layers in the subsequent stage, or may be different from the number of input layers in the subsequent stage.

A data set for each of predetermined periods until the index data reaches the predetermined target level is input as teacher data to the input layer of the auto-encoder 5310. Note that in some cases, the auto-encoder is classified as learning without teacher data. However, this example is described on the assumption that the auto-encoder corresponds to learning with teacher data in which the correct-answer label of each output parameter in the output layer is regarded as a respective one of the input parameters in the input layer, and hence the aforementioned data set is input as teach data.

Further, for the operation stage, each auto-encoder 5310 or the like may further include a final external output layer that outputs a node number having the highest certainty factor (i.e., corresponding to the index level) among the output parameters output from the intermediate layer. In this case, it is possible to perform learning so that the aforementioned teacher data has a correct-answer label for the external output layer.

By the above-described configuration, the auto-encoder 5310 can input rehabilitation data over a plurality of weeks (including data before the training is started) as a group of input parameters and output predicted index data in the first week as an output parameter of the intermediate layer (or the above-described external output layer). Note that the predicted index data may be a predicted index level of the index data. An output of the output layer in the auto-encoder 5310 is input to the auto-encoder 5311 in the subsequent stage. For this input, the auto-encoder 5311 can output predicted index data in the second week as an output parameter of the intermediate layer (or the above-described external output layer). The same applies to the subsequent weeks. That is, the learning model 5300 may have the number of auto-encoders equal to the number of predetermined periods (e.g., several weeks) for which output parameters need to be output from the intermediate layer, and may obtain an output parameter a period after each of the predetermined periods has elapsed. Note that at the time of learning, the aforementioned group of input parameters may be input to each of the auto-encoders 5310 and the like.

By the learning model 5300 in which such auto-encoders are arranged, it is possible to estimate an index level of index data such as a walking FIM that the trainee reaches, for example, in the first week, i.e., to extract the index level from the intermediate layer such as each auto-encoder 5310 as a feature of its data set.

Note that the learning model 5300 may adopt other configurations such as a perceptron having four layers or more in which the intermediate layer is not divided. However, in the case where learning is performed in the multi-layered state, the learning may not be satisfactorily performed due to the gradient vanishing problem. Therefore, the intermediate layer may be divided into three layers of auto-encoders and the learning is separately performed in each layer as in the case of the learning model 5300.

In the operation using the learning model 5300, the walking training apparatus 100 outputs rehabilitation data (without a correct-answer label) similar to that in the learning stage to the server 500, and the prediction unit 510*a* input the output rehabilitation data to the learning model 5300 and thereby obtains a prediction result. The prediction unit 510*a* summarizes the values of output parameters of all the intermediate layers and arranges the summarized values into data by which, for example, a change pattern like the one shown in FIG. 10 can be drawn, and the response processing unit 510*c* returns a command corresponding to the arranged data to the walking training apparatus 100. The walking training apparatus 100 receives the command and shows the change pattern on, for example, the management monitor 139 as shown in FIG. 10.

Further, the prediction unit 510*a* can also obtain, for the predetermined number of predetermined periods (weeks in this example) designated by the walking training apparatus 100, the value of the output parameter of the intermediate layer of the auto-encoder corresponding thereto. In this case, the response processing unit 510*c* returns a command corresponding to the obtained value to the walking training apparatus 100. Then, the walking training apparatus 100 receives the command and, for example, shows the aforementioned value (a predicted index level such as a predicted walking FIM) together with the designated predetermined number of periods on the management monitor 139.

Fourth Embodiment

Figure 14:
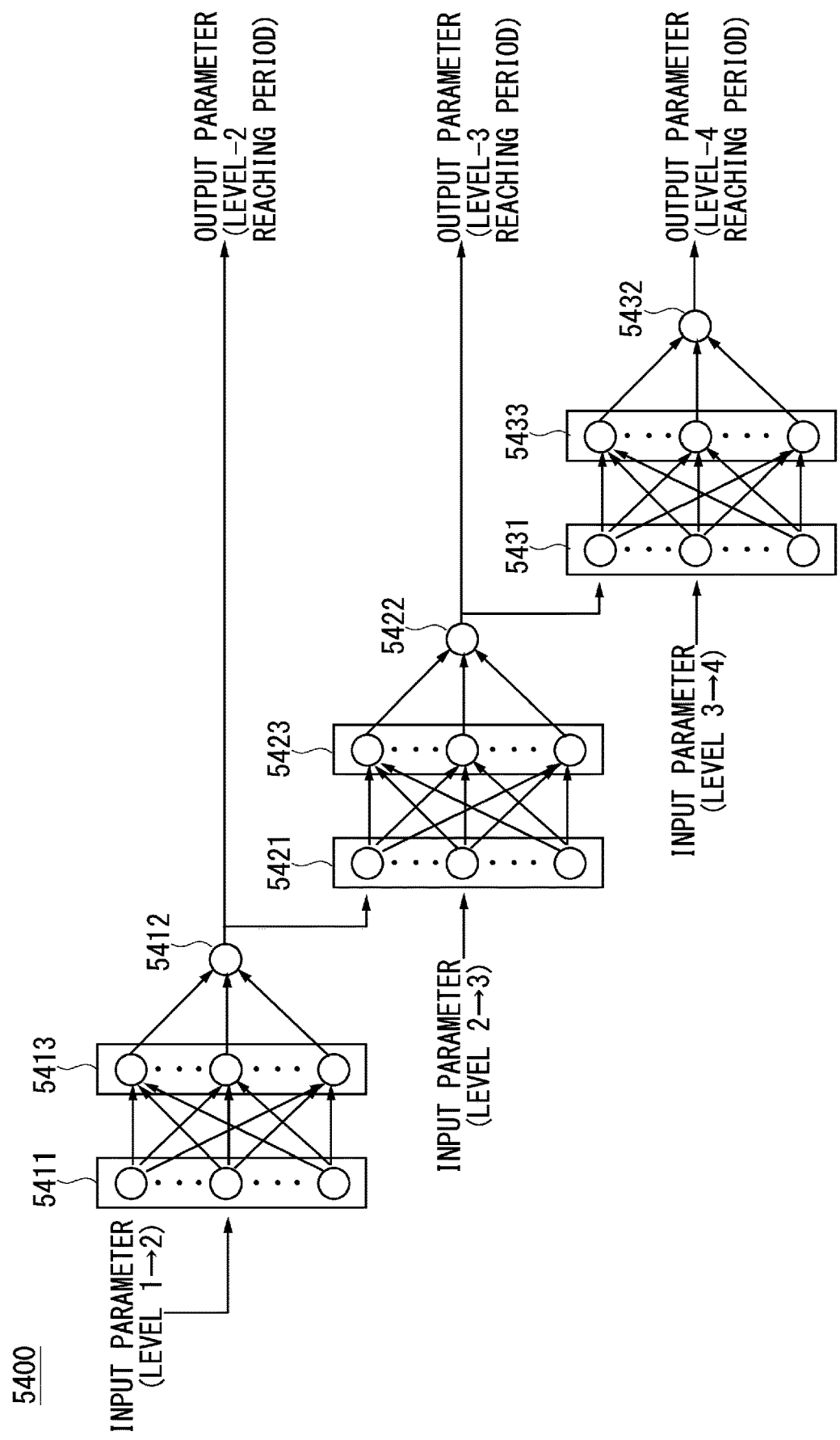
FIG. 14 shows an example of a learning model used in a rehabilitation support system according to a fourth embodiment.
Figure 15:
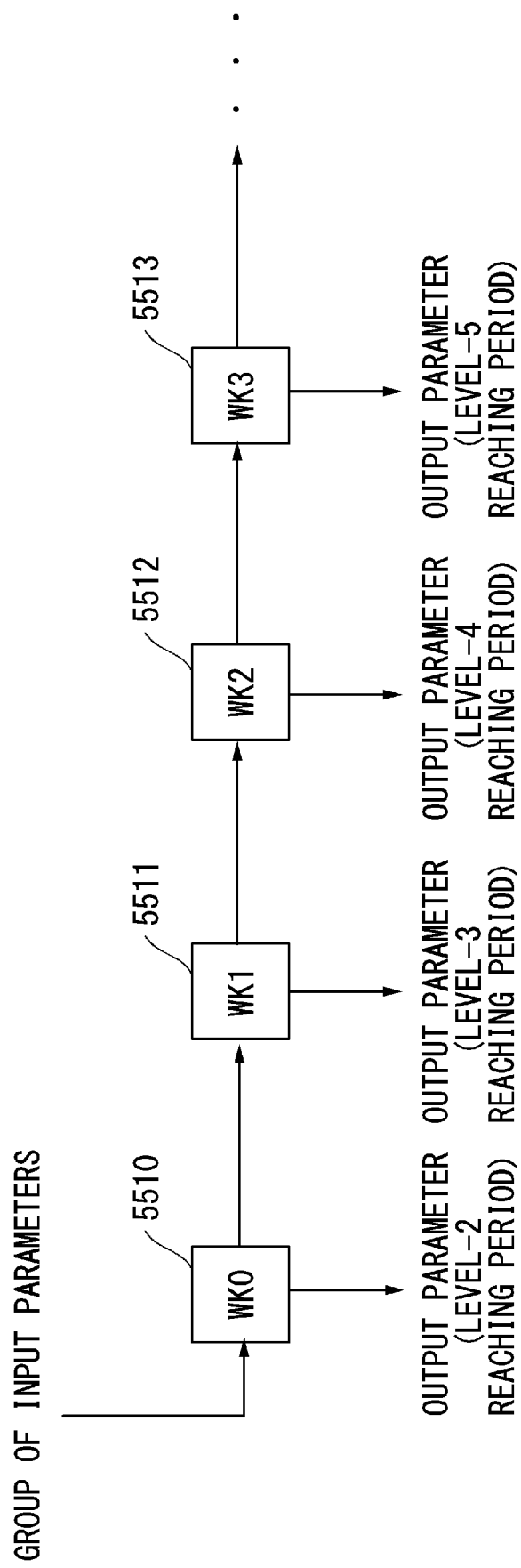
FIG. 15 shows another example of a learning model used in the rehabilitation support system according to the fourth embodiment.

A fourth embodiment will be described with reference to FIGS. 14 and 15. FIG. 14 shows an example of a learning model used in a rehabilitation support system according to this embodiment, and FIG. 15 shows another example of such a learning model. In this embodiment, a learning model having an algorithm different from those in the first to third embodiments is used. Other features and their effects are similar to those of the first to third embodiments. Further, although it is not specifically described, the various examples described above in the first to third embodiments can also be applied to this embodiment.

In this embodiment, the learning unit 510*b* generates, for each index level indicated by index data, a learning model that recursively reflects a calculation result of a one-level lower level. It should be noted that in this embodiment, the aforementioned predetermined period is regarded as a period until the index level (e.g., the value of the walking FIM) of the index data to be predicted rises (increases) by one level. Note that basically, the period until the index level increases means that the ability of the trainee 900 is improved (the level rises by predetermined levels). According to this embodiment, it is possible to construct a trained model capable of outputting a time point at which the index level increases.

In a learning model 5400 shown in FIG. 14, in a model in which the learning model 5100 is roughly expanded in the time direction, the predetermined period is defined as a period until the index level rises by one level and the output parameter is defined as each period. For example, data in a period from the index level (level) 1 to the level 2 can be data in a period until the index level of the index data to be predicted rises from the level 1 to the level 2. Similarly, data in a period from the level 2 to the level 3 can be data in a period until the index level of the index data to be predicted rises from the level 2 to the level 3. The same applies to the higher levels. Further, depending on the data set, there are cases where the index level starts from a value greater than one. In this case, they may be limited to the inputs to corresponding NNs. Note that the index data to be predicted in this example may be one of various indexes such as a walking FIM, or may include various types of indexes. In the case where one type of index is used, by constructing a learning model 5400 for each type of index, a prediction result of each type can be obtained.

The learning model 5400 is formed by connecting a first NN including an input layer 5411, an intermediate layer 5413, and an output layer including one output node 5412, and a second NN including an input layer 5421, an intermediate layer 5423, and an output layer including one output node 5422. Further, the learning model 5400 is formed by connecting an additional NN such as a third NN including an input layer 5431, an intermediate layer 5433, and an output layer including one output node 5432.

In the first NN, data in a period until the level rises from the level 1 to the level 2 is input to the input layer 5411 as an input parameter, and the period required for this rise (a Level-2 reaching period) is output from the output node 5412 as an output parameter. The output node 5412 may be a node that outputs a node number having the highest certainty factor among the nodes 5413. In the second NN, data in a period until the level rises from the level 2 to the level 3 and the output parameter from the output node 5412 are input to the input layer 5421 as an input parameter, and the period required for this rise (a Level-3 reaching period) is output from the output node 5422 as an output parameter. Note that the level-3 reaching period may be a period in which the level rises from the level 1 to the level 3. The output node 5422 may be a node that outputs a node number having the highest certainty factor among the nodes 5423. The same applies to the subsequent NNs. In the learning model 5400, the number of NNs corresponding to a predetermined number of predetermined periods (in this example, until the level rises by one level) (i.e., the number of periods included in one data set) or a number obtained by adding one to the predetermined number are provided.

In the learning stage, for example, for each NN, machine learning is performed by using teacher data like the one described in the first embodiment (teacher data for a change in the level corresponding to the NN) and by inputting data about a change in each level to the corresponding NN. In this way, a trained learning model 5400 can be generated.

Further, it is also possible to have an LSTM block by, for example, inputting an output of the output node 5412 not only to the input layer 5421 but also to an input layer that is located a predetermined number behind the input layer 5421 such as the input layer 5431 (the same applies to the subsequent output nodes).

In the operation using the learning model 5400, the walking training apparatus 100 outputs rehabilitation data (without a correct-answer label) similar to that in the learning stage to the server 500. Then, the prediction unit 510a inputs the rehabilitation data to the learning model 5200 as the data at the current level (or, in the case of data including past data, after dividing it according to the change in level), and thereby obtains a prediction result. The prediction unit 510a summarizes the values of all the output parameters and arranges the summarized values into data by which, for example, a change pattern like the one shown in FIG. 10 can be drawn, and the response processing unit 510c returns a command corresponding to the arranged data to the walking training apparatus 100. The walking training apparatus 100 receives the command and shows the change pattern on, for example, the management monitor 139 as shown in FIG. 10.

Further, the prediction unit 510a can also obtain, for the current index level included in a part of the input parameter from the walking training apparatus 100, only the value of the output parameter of the NN corresponding to the current index level (or of the NN corresponding to the current index level and the subsequent NNs). In this case, the response processing unit 510c returns a command corresponding to the obtained value to the walking training apparatus 100. Then, the walking training apparatus 100 receives the command and shows the above-described value, i.e., the predicted period until the index data reaches the next index level such as the next walking FIM (and reaches the subsequent index level) together with the current index level on the management monitor 139.

The learning model 5500 shown in FIG. 15 is a model in which auto-encoders 5510, 5511, 5512, 5513, . . . are arranged in a manner similar to that in the learning model 5300 shown in FIG. 13. It should be noted that in the learning model 5500, in the learning model 5300, it is assumed that an output parameter from the intermediate layer of each auto-encoder is a predetermined number of predetermined periods such as the number of weeks in which the index level changes. For example, it is assumed that it is a period until the output parameter from the intermediate layer of the auto-encoder 5510 reaches from the index level 1 to the level 2 (the number of weeks), and it is a period until the output parameter from the intermediate layer of the auto-encoder 5511 reaches from the index level 2 to the level 3 (the number of weeks or the cumulative number of weeks up to the present time).

By constructing the learning model 5500 having the above-described configuration, it is possible to estimate the number of predetermined periods (the number of weeks) in which the index level of the index data such as the value of the walking FIM does not further increase. That is, the learning model 5300 can extract such a number of predetermined periods from the intermediate layer of each auto-encoder 5310 or the like as a feature of the input data set.

Note that similarly to the application example of the learning model 5300, that the learning model 5500 may adopt other configurations such as a perceptron having four layers or more in which the intermediate layer is not divided. However, in the case where learning is performed in the multi-layered state, the learning may not be satisfactorily performed due to the gradient vanishing problem. Therefore, the intermediate layer may be divided into three layers of auto-encoders and the learning is separately performed in each layer as in the case of the learning model 5500.

As described above, in this embodiment, it is possible to construct a trained model that outputs a period until the index level increases (a time point at which the index level increases). Further, in the operation stage, it is possible to show such a period until the index level increases or show a change pattern from its result. Note that the above description has been given on the assumption that an increase in the index level is a change in the direction in which the result of the training is improved. However, depending on the index data, there are cases where a decrease in the index level is a change in the direction in which the result of the training is improved. Therefore, in this embodiment, it is considered that the learning unit 510b generates, for each index level indicated by the index data, a learning model that recursively reflects a calculation result of one-level-different level.

Fifth Embodiment

In the first to fourth embodiments, examples in which the server 500 includes the learning unit 510b and the server 500 generates a trained model are described. In contrast, in this embodiment, the learning unit and the pre-processing unit are provided on the walking training apparatus 100 side (e.g., in the overall control unit 210). A rehabilitation support system according to this embodiment needs to include only the walking training apparatus 100. However, in this case, it is desirable to configure the rehabilitation support system so that it can collect rehabilitation data from other walking training apparatuses in order to increase the amount of rehabilitation data collected in the learning stage.

Further, in the first to fourth embodiments, regarding the operation stage, examples in which the trained model is provided in the server 500, and the walking training apparatus 100 transmits rehabilitation data to the server 500 and receives its response from the server 500 are shown. However, the present disclosure is not limited to such examples. For example, the trained model may be incorporated on the walking training apparatus 100 side (e.g., in a storage unit disposed in the overall control section 210). Therefore, the walking training apparatus 100 may include a storage unit that stores the trained model. Further, although it is not specifically described, the various examples described above in the first to fourth embodiments can also be applied to this embodiment.

Alternative Example

Each of the above-described embodiments is described by using an example in which the trainee 900 is a hemiplegic patient who has a disorder in one of his/her legs. However, the walking training apparatus 100 can also be applied to a patient whose legs are both paralyzed. In this case, the patient performs training with walking assistance apparatuses 120 attached to both legs. In this case, abnormal walking may be evaluated for each of the diseased legs. The degree of recovery can be individually determined for each diseased leg by independently evaluating abnormal walking for each leg.

Further, although it is not shown in the drawings, the walking training apparatus may be an apparatus that is not equipped with the treadmill 131 of the walking training apparatus 100 shown in FIG. 1, so that the trainee 900 can actually move in the space surrounded by the frame 130. In this case, the frame 130 may be formed so that it has a large length in the traveling direction. Further, it may adopt a configuration in which the harness pulling unit 112, the front pulling unit 135, and the rear pulling unit 137 are moved along guide rails by a motor(s) (not shown) as the trainee 900 moves. Since the trainee 900 actually moves relative to the floor surface, he/she can feel a sense of accomplishment of rehabilitation training more effectively. Needless to say, the walking training apparatus is not limited to these configuration examples.

Further, the target level and the predetermined level described in each embodiment can be handled as examples of the target degree and the predetermined degree, respectively. That is, the level may be an example of the degree. As another example, the target degree and the predetermined degree may be a target value for the index value indicated by the index data and a predetermined value for the index value indicated by the index data, respectively. Although its description is omitted, levels related to other values can be similarly handled as examples of the degrees.

Further, each of the above-described embodiments is described on the assumption that the training staff member 901 is a human being. However, as a substitute, a non-human training assistant (e.g., a mechanical or artificial training assistant) may be employed. As the artificial training assistant, there are various types of assistants such as a humanoid robot, a voice assistant program, and a display assistant program. As an example in which a voice assistant program assists the trainee by voice, it is possible to give encouraging talks such as "Please lean your upper body further to the right", "Please hold the handrails", and "Please slow down your walking speed".

When the training assistant is a computer program, it can be incorporated in the walking training apparatus 100 in an executable manner. Alternatively, the program may also be incorporated, in an executable manner, in a portable terminal such as a mobile phone (including a smartphone), a mobile PC, or an external server capable of communicating with the walking training apparatus 100. Further, the artificial training assistant may also include a program with artificial intelligence (an AI program).

Further, a plurality of artificial training assistants may be made available when walking training is performed in the walking training apparatus 100, and each of them may be separately managed in a distinguishable manner. That is, even when the training assistant is an artificial training assistant, the training assistant can be distinguished from other training assistants as in the case of the human training staff member.

Further, when an artificial training assistant is used, examples of the data (the assistant data) related to the artificial training assistant corresponding to the data related to the training staff member 901 in the above-described item (4) include the below-shown data. The examples include functions (such as a voice assist function and an assistance function using a video display) of the artificial training assistant (the program), and a name and a version of the program. Further, when the program is a type of an AI program that learns during its operation, the examples include a learning algorithm, a degree of learning, a learning time, and the number of times of learning.

Further, in the case where a plurality of training assistants (irrespective of whether the assistant is a human assistant or a non-human assistant) simultaneously assist the rehabilitation, the rehabilitation data may include assistant data of the plurality of assistants as in the case of the plurality of human training staff members as described above. Further, each assistant data may also include information indicating whether the assistant is a main training assistant or an assistance training assistant. In addition to or instead of the aforementioned information, each assistant data may include information indicating what kind of assistance is provided.

A notification will be described. For example, when a notification to an artificial training assistant, rather than the human assistant such as the training staff member 901, is required, the notification control unit 210*d* may notify the artificial training assistant. The notification may be directly provided through communication. Alternatively, the notification may be provided by a video image or a voice as in the case of the human assistant and the video or voice notification may be detected by the artificial training assistant. Further, the artificial training assistant may be configured so as to be able to change the setting or the like of the walking training apparatus 100 through communication or a direct-touch operation.

Further, a rehabilitation support apparatus described in each embodiment may be formed as a rehabilitation support system by using a plurality of apparatuses. Similarly, the walking training apparatus may be formed as a walking training system by using a plurality of apparatuses, and the training support apparatus may be formed as a training support system by using a plurality of apparatuses. Further, for example, a server (a server apparatus) described in each embodiment may not be equipped with the learning apparatus but may be equipped only with the trained model. Further, the server may be equipped with all of or only some of the functions of the learning apparatus. Further, a server apparatus described in each embodiment may include at least some of the functions and parts described as the functions and parts of the rehabilitation support apparatus.

Further, as described above, a rehabilitation support apparatus according to each embodiment may be an apparatus for supporting other kinds of rehabilitation, i.e., rehabilitation other than the walking training, or for supporting training other than the rehabilitation. In such a case, the learning apparatus according to each embodiment may be a learning apparatus that generates a trained model that is adapted to that apparatus. For example, it is possible to use input parameters and output parameters corresponding to the type of the rehabilitation or the type of the training. Examples of the training other than the rehabilitation include exercises such as walking and running and training. Further, a training support apparatus corresponding to the type of the training can be used. Further, the index data in the case of the training other than the rehabilitation may be data indicating the degree of an improvement in a physical function of the trainee instead of the degree of recovery of the trainee. The degree of an improvement in a physical function may include an improvement in a muscle strength by an exercise or the like and/or an improvement in endurance. Further, even when the training is the rehabilitation, the index data may be data indicating the degree of an improvement in a physical function of the trainee. In this case, the degree of an improvement in a physical function may include the degree of recovery by the rehabilitation or the like. Further, in the case of the training other than the rehabilitation, the rehabilitation data can be referred to as training data.

Further, the above-described rehabilitation support apparatus or the server apparatus may have a hardware configuration including, for example, a processor, a memory, and a communication interface. These apparatuses are implemented by making the processor load and execute a program stored in the memory.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A learning system comprising:
a walking training apparatus and a walking assistance apparatus used by a current trainee, and
a processor programmed to:
receive rehabilitation data for predetermined periods, the rehabilitation data being associated with a plurality of past trainees, the rehabilitation data including at least index data, trainee data, and training data of each trainee,
the index data indicating a physical symptom, a physical ability, and a degree of recovery of each trainee,
the trainee data indicating an age, a gender, a physique, a preference, and a personality of each trainee,
the training data being generated by the plurality of past trainees when the past trainees each used the walking training apparatus and the walking assistance apparatus and including (i) information that indicates a frequency with which the walking assistance apparatus attachable to a lower leg of one of the past trainees is used with the walking training apparatus when the past trainees perform the rehabilitation, (ii) setting parameters in the walking training apparatus that are used when the past trainees perform the rehabilitation, and (iii) detection data detected by sensors provided in the walking training apparatus when the past trainees perform the rehabilitation, and
generate, by using machine learning on the received rehabilitation data that is from the plurality of past trainees, a learning model for predicting a change in the index data for the current trainee, and by using, as teacher data, data for past trainees obtained in a period until the index data reaches a predetermined target level, and
the learning model is configured to output as the change in the index data information indicating a change pattern that represents how an estimated trajectory of a walking-related parameter that represents walking ability for the current trainee changes with respect to time over a future time period,
wherein the walking assistance apparatus is attachable to a lower leg of the current trainee when the current trainee performs rehabilitation, and
wherein the walking training apparatus and the walking assistance apparatus used by the current trainee obtain the index data for the current trainee as the current trainee performs rehabilitation.

2. The learning system according to claim 1, wherein the processor is further programmed to extract, from rehabilitation data of the plurality of past trainees, rehabilitation data of a past trainee whose condition indicated by the index data at an early stage of the training is at a predetermined level, and
generate the learning model for the current trainee having the predetermined level by using the rehabilitation data as an input.

3. The learning system according to claim 2, wherein the processor is further programmed to extract rehabilitation data of the past trainee of which a combination of the index data at the early stage of the training and the index data at the time when it is at the predetermined level is a predetermined combination.

4. The learning system according to claim 1, wherein the learning model is a model for predicting a pattern of changes in the index data in which the index data gets closer to the predetermined target level.

5. The learning system according to claim 1, wherein the learning model is a model in which, in each of index levels indicated by the index data, a result of calculation at a one-level-different level is recursively reflected.

6. The learning system according to claim 1, wherein the learning model is a model including an RNN (Recurrent Neural Network).

7. The learning system according to claim 6, wherein the learning model is a model including an LSTM (Long Short-Term Memory) block.

8. The learning system according to claim 1, wherein the walking assistance apparatus is a boot configured to be worn on the lower leg of a trainee.

9. The learning system according to claim 8, wherein the walking assistance apparatus comprises an upper leg frame and a lower leg frame that is rotatably connected to the upper leg frame.

10. The learning system according to claim 9, wherein the walking assistance apparatus comprises a motor configured to drive the upper leg frame and the lower leg frame to move relative to each other.

11. The learning system according to claim 1, wherein walking training apparatus includes a treadmill, and the training data includes information related to operation of the treadmill.

12. The learning system according to claim 1, wherein walking training apparatus includes a treadmill and a harness configured to support a trainee, and the training data includes information related to operation of the treadmill.

13. The learning system according to claim 1, wherein the setting parameters further comprise a level of assistance for assisting motion of a joint by the walking assistance apparatus.

14. The learning system according to claim 1, wherein walking training apparatus includes a treadmill, and the setting parameters further comprise a treadmill speed of the treadmill.

15. A learning method that is implemented with a walking training apparatus and a walking assistance apparatus used by a current trainee, and comprising a learning step of receiving rehabilitation data for predetermined periods, the rehabilitation data being associated with a plurality of past trainees, the rehabilitation data including at least index data, trainee data, and training data of each trainee, the index data indicating a physical symptom, a physical ability, and a degree of recovery of each trainee, the trainee data indicating an age, a gender, a physique, a preference, and a personality of each trainee, the training data being generated by the plurality of past trainees when the past trainees each used the walking training apparatus and the walking assistance apparatus and including (i) information that indicates a frequency with which the walking assistance apparatus attachable to a lower leg of one of the past trainees is used with the walking training apparatus when the past trainees perform the rehabilitation, (ii) setting parameters in the walking training apparatus that are used when the past trainees perform the rehabilitation, and (iii) detection data detected by sensors provided in the walking training apparatus when the past trainees perform the rehabilitation, wherein in the learning step, the learning model is generated by using machine learning on the received rehabilitation data that is from the plurality of past trainees, to generate the learning model for predicting a change in the index data for the current trainee, and by using as teacher data for past trainees, data obtained in a period until the index data reaches a predetermined target level, and the learning model outputs as the change in the index data information indicating a change pattern that represents how an estimated trajectory of a walking-related parameter that represents walking ability for the current trainee changes with respect to time over a future time period, wherein the walking assistance apparatus is attachable to a lower leg of the current trainee when the current trainee performs rehabilitation, and wherein the walking training apparatus and the walking assistance apparatus used by the current trainee obtain the index data for the current trainee as the current trainee performs rehabilitation.

16. A method for supporting rehabilitation performed in the walking training apparatus capable of accessing a trained model, the trained model being the learning model trained by the learning method according to claim 15, the method comprising:

a prediction step of inputting rehabilitation data including at least the index data and the training data of the current trainee who starts or is performing training to the trained model, and thereby predicting the change in index data; and a presentation step of showing the change in index data predicted in the prediction step.

* * * * *